(12) United States Patent
Eaton

(10) Patent No.: US 10,420,919 B2
(45) Date of Patent: Sep. 24, 2019

(54) INTRODUCER WITH DYNAMIC DILATOR AND METHODS OF USING THE SAME

(71) Applicant: Elizabeth A. Eaton, Bloomington, IN (US)

(72) Inventor: Elizabeth A. Eaton, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 611 days.

(21) Appl. No.: 15/135,963

(22) Filed: Apr. 22, 2016

(65) Prior Publication Data

US 2016/0310166 A1   Oct. 27, 2016

Related U.S. Application Data

(60) Provisional application No. 62/152,074, filed on Apr. 24, 2015.

(51) Int. Cl.
| | | |
|---|---|---|
| *A61M 29/02* | (2006.01) | |
| *A61M 25/00* | (2006.01) | |
| *A61M 25/06* | (2006.01) | |

(52) U.S. Cl.
CPC ........ *A61M 29/02* (2013.01); *A61M 25/0074* (2013.01); *A61M 2025/0681* (2013.01); *A61M 2025/0687* (2013.01)

(58) Field of Classification Search
CPC .............. A61M 29/02; A61M 25/0074; A61M 2025/0681; A61M 2025/0687
See application file for complete search history.

(56) References Cited

U.S. PATENT DOCUMENTS

| | | |
|---|---|---|
| 5,015,239 A | 5/1991 | Browne |
| 5,183,464 A | 2/1993 | Dubrul et al. |
| 5,201,756 A | 4/1993 | Horzewski et al. |
| 5,431,676 A | 7/1995 | Dubrul et al. |
| 5,573,517 A | 11/1996 | Bonutti et al. |
| 5,817,127 A | 10/1998 | Borodulin et al. |
| 5,885,217 A | 3/1999 | Gisselberg et al. |
| 6,024,763 A | 2/2000 | Lenker et al. |
| 6,120,480 A | 9/2000 | Zhang et al. |
| 6,589,262 B1 | 7/2003 | Honebrink et al. |
| 6,616,678 B2 | 9/2003 | Nishtala et al. |

(Continued)

FOREIGN PATENT DOCUMENTS

| | | |
|---|---|---|
| EP | 2444115 | 4/2012 |
| WO | WO9730746 | 8/1997 |

(Continued)

*Primary Examiner* — Lauren P Farrar
(74) *Attorney, Agent, or Firm* — Buchanan Van Tuinen LLC

(57) ABSTRACT

Medical devices and methods of using medical devices are described herein. More particularly, the disclosure relates to introducers suitable for providing access to a body vessel and methods of using introducers. An example introducer comprises a sheath and a dilator moveably disposed within the sheath. The distal end of the dilator has a closed configuration and an open configuration and movement between the open and closed configurations can be accomplished by applying a proximally-directed force on the sheath such that the sheath moves in a proximal direction relative to the dilator.

20 Claims, 9 Drawing Sheets

(56) References Cited

U.S. PATENT DOCUMENTS

| | | |
|---|---|---|
| 7,226,464 B2 | 6/2007 | Garner et al. |
| 7,655,021 B2 | 2/2010 | Brasington et al. |
| 8,021,387 B2 | 9/2011 | Keidar |
| 8,262,619 B2 | 9/2012 | Chebator et al. |
| 8,282,664 B2 | 10/2012 | Nance et al. |
| 8,597,454 B2 | 12/2013 | Parker et al. |
| 9,211,389 B2 | 12/2015 | Eaton |
| 2002/0193822 A1 | 12/2002 | Hung et al. |
| 2004/0181273 A1 | 9/2004 | Brasington et al. |
| 2008/0142005 A1* | 6/2008 | Schnell .............. A61B 17/3415 128/200.26 |
| 2009/0105652 A1 | 4/2009 | Beal et al. |
| 2013/0041398 A1 | 2/2013 | Goddard et al. |
| 2013/0184736 A1* | 7/2013 | Aman ................... A61M 29/00 606/191 |
| 2013/0261399 A1 | 10/2013 | Lenker et al. |
| 2015/0250991 A1* | 9/2015 | Silvestro ............... A61M 29/02 606/194 |

FOREIGN PATENT DOCUMENTS

| | | |
|---|---|---|
| WO | WO2013106134 | 7/2013 |
| WO | WO2013130464 | 9/2013 |

\* cited by examiner

US 10,420,919 B2

INTRODUCER WITH DYNAMIC DILATOR AND METHODS OF USING THE SAME

RELATED APPLICATION

This application claims the benefit of U.S. Provisional Application No. 62/152,074 filed Apr. 24, 2015. The entire disclosure of this related application is hereby incorporated into this disclosure by reference.

FIELD

The disclosure relates generally to the field of medical devices. More particularly, the disclosure relates to introducers suitable for providing access to a body vessel, such as a blood vessel, and methods of using an introducer.

BACKGROUND

Various clinical procedures exist for introducing medical devices, such as stents, valves, filters, and other intraluminal medical devices, into a body vessel. For example, a percutaneous introduction technique typically includes the insertion of a hollow needle through the skin and into a desired blood vessel, which creates a puncture site. A guidewire is then advanced through the needle and into the blood vessel via the puncture site. The needle is subsequently withdrawn, leaving the guidewire partially disposed within the blood vessel and partially disposed outside the body. A dilator is then advanced over the guidewire into the blood vessel such that gradual, proximally-directed insertion of the dilator progressively enlarges the diameter of the puncture site until it is suitable for advancement of a sheath having a lumen into the blood vessel. The sheath is then advanced over the guidewire and into the blood vessel. Next, the dilator is removed to leave the sheath and guidewire in place, which can then be used for insertion of a catheter or other medical device into the blood vessel via the lumen of the sheath.

Removal of the dilator can add time and complexity to a procedure where the loss of established access is a concern. In addition, the act of removing a dilator can change the position of the distal end of the sheath disposed within the body vessel and/or can change the position of the distal end of the guidewire, which can create inaccuracy in the position of a treatment being delivered and/or performed, and may necessitate additional navigation of the sheath and/or guidewire in an attempt to eliminate or reduce such inaccuracy. For example, if the position of the distal end of the guidewire has been altered during removal of the dilator, additional imaging may be required to confirm or adjust the guidewire's placement. A need exists, therefore, for improved devices and methods useful in the introduction of medical devices into body vessels.

BRIEF SUMMARY OF DESCRIBED EMBODIMENTS

Various example introducers and methods of using introducers are described herein.

An example introducer comprises a sheath and a dilator. The sheath has a sheath proximal end, a sheath distal end, a sheath main body that extends between the sheath proximal end and the sheath distal end, and a sheath longitudinal axis. The sheath main body defines a sheath lumen. The dilator is disposed within the sheath lumen and is moveable between a closed configuration and an open configuration. The dilator has a dilator proximal end, a dilator distal end, a dilator main body that extends between the dilator proximal end and the dilator distal end, and defines a dilator inner passageway, a first lateral portion, and a second lateral portion. The first and second lateral portions are opposably positioned with respect to the sheath longitudinal axis. The first lateral portion has a first lateral portion thickness that tapers from a first location between the dilator proximal end and the dilator distal end toward the dilator distal end. The second lateral portion has a second lateral portion thickness that tapers from a second location between the dilator proximal end and the dilator distal end toward the dilator distal end. The dilator has a first outside diameter at the distal end when the dilator is in the closed configuration and a second outside diameter at the distal end when the dilator is in the open configuration. The second outside diameter is greater than the first outside diameter. Proximally-directed movement of the sheath along the sheath longitudinal axis relative to the dilator results in movement of the dilator from the closed configuration to the open configuration and radially-outward movement of the first and second lateral portions relative to the sheath longitudinal axis.

Another example introducer comprises a sheath and a dilator. The sheath has a sheath proximal end, a sheath distal end, a sheath main body that extends between the sheath proximal end and the sheath distal end, a sheath length that extends from the sheath proximal end to the sheath distal end, and a sheath longitudinal axis. The sheath main body defines a sheath lumen and has a first outside diameter. The dilator is disposed within the sheath lumen and is moveable between a closed configuration and an open configuration. The dilator has a dilator proximal end, a dilator distal end, a dilator main body that extends between the dilator proximal end and the dilator distal end, a dilator length that extends from the dilator proximal end to the dilator distal end, and defines a dilator inner passageway, a first lateral portion, and a second lateral portion. The dilator length is greater than the sheath length. The first and second lateral portions are opposably positioned with respect to the sheath longitudinal axis. The first lateral portion has a first lateral portion thickness that tapers from a first location between the dilator proximal end and the dilator distal end toward the dilator distal end. The second lateral portion has a second lateral portion thickness that tapers from a second location between the dilator proximal end and the dilator distal end toward the dilator distal end. The dilator has a second outside diameter at the distal end when the dilator is in the closed configuration and a third outside diameter at the distal end when the dilator is in the open configuration. The second outside diameter is greater than the first outside diameter and the third outside diameter. Proximally-directed movement of the sheath along the sheath longitudinal axis relative to the dilator results in movement of the dilator from the closed configuration to the open configuration and radially-outward movement of the first and second lateral portions relative to the sheath longitudinal axis. In the closed configuration, the first lateral portion and the second lateral portion are adjacent and contact each other and in the open configuration the first lateral portion and second lateral portion are spaced from each other with respect to the sheath longitudinal axis.

Another example introducer comprises a sheath and a dilator. The sheath has a sheath proximal end, a sheath distal end, a sheath main body that extends between the sheath proximal end and the sheath distal end, a sheath length that extends from the sheath proximal end to the sheath distal end, and a sheath longitudinal axis. The sheath main body defines a sheath lumen and having a first outside diameter. The dilator is disposed within the sheath lumen and is moveable between a closed configuration and an open configuration. The dilator has a dilator proximal end, a dilator distal end, a dilator main body that extends between the dilator proximal end and the dilator distal end, a dilator length that extends from the dilator proximal end to the dilator distal end, and defines a dilator inner passageway, a first lateral portion, and a second lateral portion. The dilator length is greater than the sheath length. The first and second lateral portions are opposably positioned with respect to the sheath longitudinal axis and cooperatively define an opening on the dilator distal end when the dilator is in the closed configuration. The first lateral portion has a first lateral portion inner surface and a first lateral portion thickness that tapers from a first location between the dilator proximal end and the dilator distal end toward the dilator distal end. The first lateral portion inner surface is disposed on a first plane that is substantially parallel to the sheath longitudinal axis when the dilator is in the closed configuration. The second lateral portion has a second lateral portion inner surface and a second lateral portion thickness that tapers from a second location between the dilator proximal end and the dilator distal end toward the dilator distal end. The second lateral portion inner surface is disposed on a second plane that is substantially parallel to the sheath longitudinal axis when the dilator is in the closed configuration. The dilator has a second outside diameter at the distal end when the dilator is in the closed configuration and a third outside diameter at the distal end when the dilator is in the open configuration. The second outside diameter is greater than the first outside diameter and the third outside diameter. Proximally-directed movement of the sheath along the sheath longitudinal axis relative to the dilator results in movement of the dilator from the closed configuration to the open configuration and radially-outward movement of the first and second lateral portions relative to the sheath longitudinal axis. In the closed configuration, the first lateral portion and the second lateral portion are adjacent and contact each other and in the open configuration the first lateral portion and second lateral portion are spaced from each other with respect to the sheath longitudinal axis.

Additional understanding of the invention can be obtained with review of the description of example embodiments, below, and the appended drawings.

DETAILED DESCRIPTION OF EXAMPLE EMBODIMENTS

Figure 1:
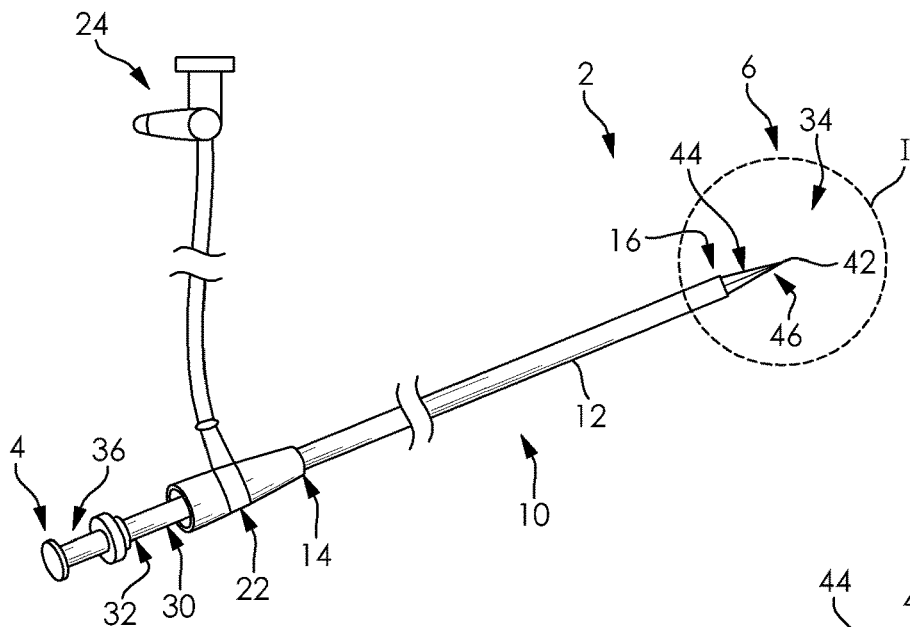
FIG. 1 is a perspective view of an embodiment of an introducer.

The following detailed description and appended drawings describe and illustrate various example introducers. In addition, example methods of using an introducer are described and illustrated. The description and drawings of these examples are provided to enable one skilled in the art to make one or more example introducers and/or practice a method of using an introducer. They are not intended to limit the scope of the claims in any manner.

FIGS. 1, 2, 3, 4, 5A, and 5B illustrate a first example introducer 2. The introducer 2 has a proximal end 4, a distal end 6, and includes a sheath 10 and a dilator 30. The sheath 10 is elongate and tubular and has a main body 12, a proximal end 14, a distal end 16, a longitudinal axis 17, and defines a lumen 18 and an inner surface 20. The longitudinal axis 17 extends continuously through the center of the lumen 18 from the proximal end 14 to the distal end 16. Each of the main body 12, lumen 18, and the inner surface 20 extends from the proximal end 14 to the distal end 16. The main body 12 has a thickness that varies along the length of the sheath 10 such that a distal portion of the sheath 10 tapers from a location between the proximal end 14 and the distal end 16 to the distal end 16. In the illustrated embodiment, a hub 22 is disposed on the proximal end 14 of the sheath 10 and is connected to a valve apparatus 24. While the hub 22 and valve apparatus 24 are illustrated in the example embodiment, alternative embodiments can omit the inclusion of a hub and a valve apparatus can be directly connected to the sheath 10. Alternatively, both the hub 22 and valve apparatus 24 can be omitted from an introducer.

While the sheath 10 has been described as elongate and tubular and as having a particular structural arrangement, a sheath can have any suitable structural arrangement. Skilled artisans will be able to select a suitable structural arrangement for a sheath according to a particular embodiment based on various considerations, including the structural arrangement of a dilator included in an introducer of which the sheath is a component. Example structural arrangements considered suitable for a sheath include sheaths that omit the inclusion of a tapered distal end, sheaths that have a constant, or substantially constant, outside diameter along a portion, or the entirety, of their length, sheaths that have an outside diameter that varies along their length, sheaths in which a lumen defined by the sheath has a constant, or substantially constant, inside diameter along a portion, or the entirety, of its length, sheaths in which a lumen defined by the sheath has an inside diameter that varies along its length, sheaths that define one or more apertures, or pores, along a portion, or the entirety, of their length, sheaths that define one or more slits along a portion, or the entirety, of their length, and any other structural arrangement considered suitable for a particular application. For example, a sheath, such as those described herein, can include a completely circumferentially closed member, a member that defines a slit along the entirety, or a portion, of its length, a member that defines one or more, or a plurality, of perforations along its length, and any other structural configuration considered suitable for a particular embodiment.

Figure 5A:
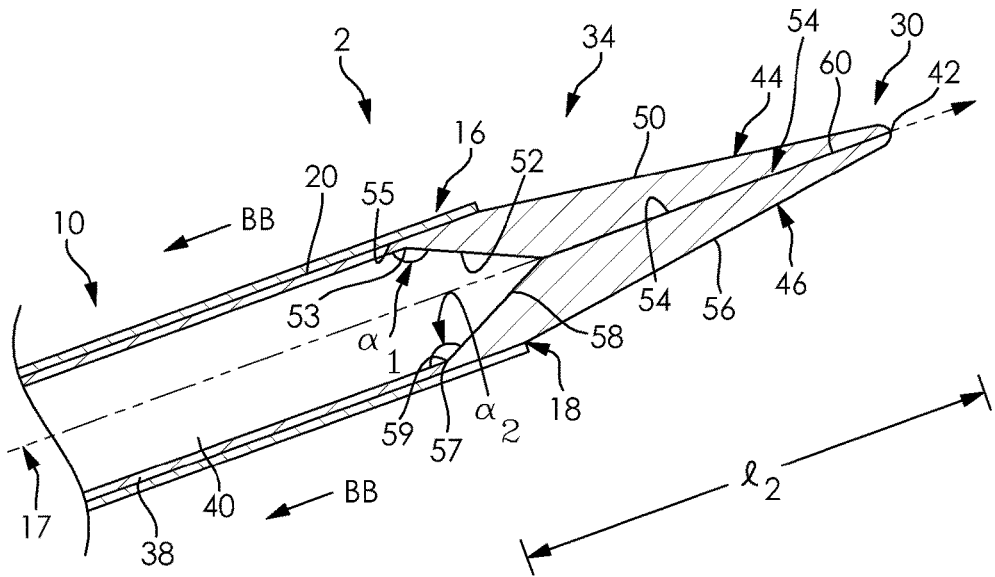
FIG. 5A is a partial sectional view of the distal end of the introducer illustrated in FIG. 3 taken along line AA-AA. The distal end of the dilator is illustrated in the closed configuration.
Figure 5B:
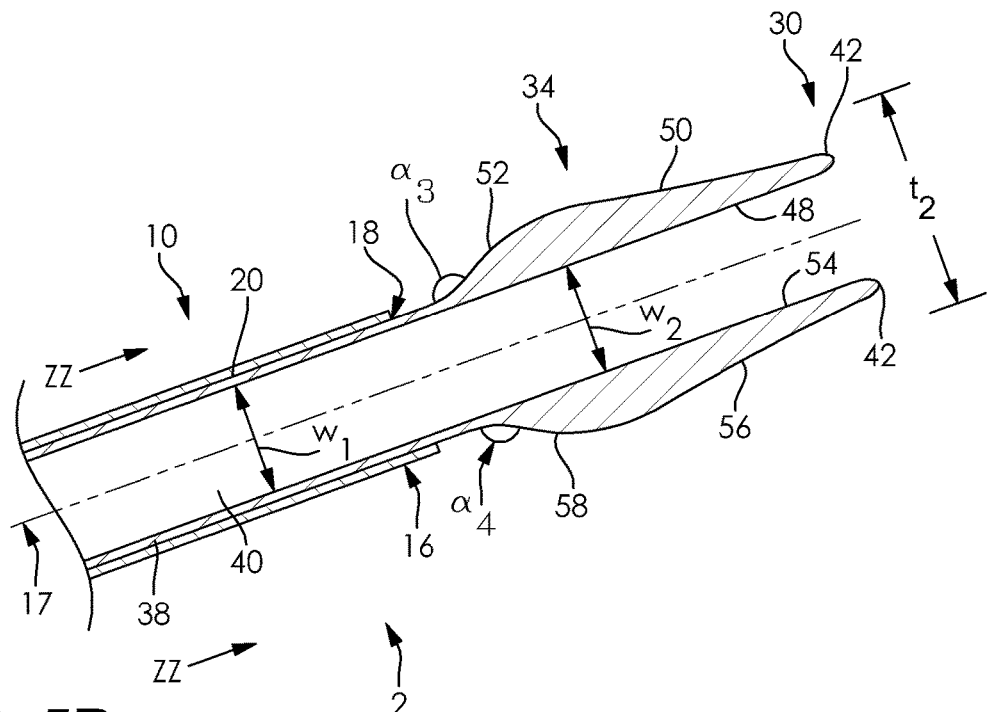
FIG. 5B is a view of the introducer illustrated in FIG. 5A in which the distal end of the dilator is illustrated in the open configuration.

The dilator 30 is moveably disposed within the lumen 18 (e.g., dilator 30 is slidably disposed within lumen 18) of the sheath 10 and has a proximal end 32, a distal end 34, a handle 36, and a main body 38 that defines an inner passageway 40 and a distal tip 42. Each of the main body 38 and the inner passageway 40 extends between the proximal end 32 and the distal end 34. The dilator 30 has an open configuration, as illustrated in FIG. 5A, and a closed configuration, as illustrated in FIG. 5B.

The distal end 34 of the dilator 30 has a first lateral portion 44 and a second lateral portion 46. The first and second lateral portions 44, 46 can be formed by cutting two sides of the main body 38 along a portion of the length of the dilator 30 from the distal end 34 toward the proximal end 32. Alternatively, the first and second lateral portions of a dilator can be formed by cutting two sides of the main body of a dilator along the entire length of the main body or by attaching (e.g., using adhesive) two separate members having a structural configuration similar to the first and second lateral portions described herein to the distal end of a member (e.g., tubular member, an elongate member with one or more slits along a portion, from the distal end toward the proximal end, or the entirety of its length) to form a dilator. In an alternative embodiment, a sheath and/or dilator can include a valve member (e.g., attached to the proximal end of the sheath and/or dilator, or disposed within the inner passageway defined by the sheath and/or dilator) to prevent fluid from passing through the dilator during use. The first and second lateral portions 44, 46 are opposably positioned (e.g., substantially opposite one another) with respect to the longitudinal axis 17 of the sheath 10 when the distal end 34 of the dilator 30 is in the closed configuration. The first lateral portion 44 has a first inner surface 48, a first outer surface 50, and a first transition portion 52. The second lateral portion 46 has a second inner surface 54, a second outer surface 56, and a second transition portion 58. The first and second transition portions 52, 58 have first and second transition points 53, 59, respectively, which are adjacent the main body 38. Each of the first lateral portion 44 and the second lateral portion 46 has a thickness that tapers from a location between the proximal end 32 and the distal end 34 toward the distal end 34 of the dilator 30. When the dilator 30 is in the closed configuration, the entire first inner surface 48 and the entire second inner surface 54 contact one another along the longitudinal axis 17 of the sheath 10 to cooperatively define an interface 60. The interface 60 is disposed on the longitudinal axis 17 from the distal tip 42 to a split point 43, which is the most proximal point at which first and second lateral portions 44, 46 contact one another. While the dilator 30 has been described as having a first lateral portion 44 and a second lateral portion 46 and open and closed configurations, a dilator can have any suitable number of lateral portions and any suitable number of configurations. Skilled artisans will be able to determine a suitable number of lateral portions to include on a dilator and a suitable number of configurations for a dilator based on various considerations, including the dimensions of a sheath and a dilator included in an introducer, the specific procedure for which an introducer is designed, and the materials that form an introducer.

While the entire first and second inner surfaces 48, 54 have been described as contacting one another along the longitudinal axis 17 of the sheath 10, any suitable length of the first inner surface of a first lateral portion can contact the second inner surface of a second lateral portion. Skilled artisans will be able to determine how best to position the first and second inner surfaces of a dilator when the distal end of the dilator is in the closed configuration based on various considerations, including the dimensions of a sheath and dilator included in an introducer, the specific procedure for which an introducer is designed, and the materials that form an introducer. Example configurations considered suitable between the first inner surface and second inner surface of a dilator include the first inner surface of a first lateral portion and the second inner surface of a second lateral portion intermittently contacting one another when the distal end of the dilator is in the closed configuration, the first inner surface of a first lateral portion and the second inner surface of a second lateral portion being spaced apart from one another with respect to the longitudinal axis of a sheath such that they do not contact when the distal end of the dilator is in the closed configuration, the first inner surface of a first lateral portion and the second inner surface of a second lateral portion contacting one another along an axis other than the longitudinal axis of a sheath, and any other configuration considered suitable for a particular embodiment.

Figure 2:
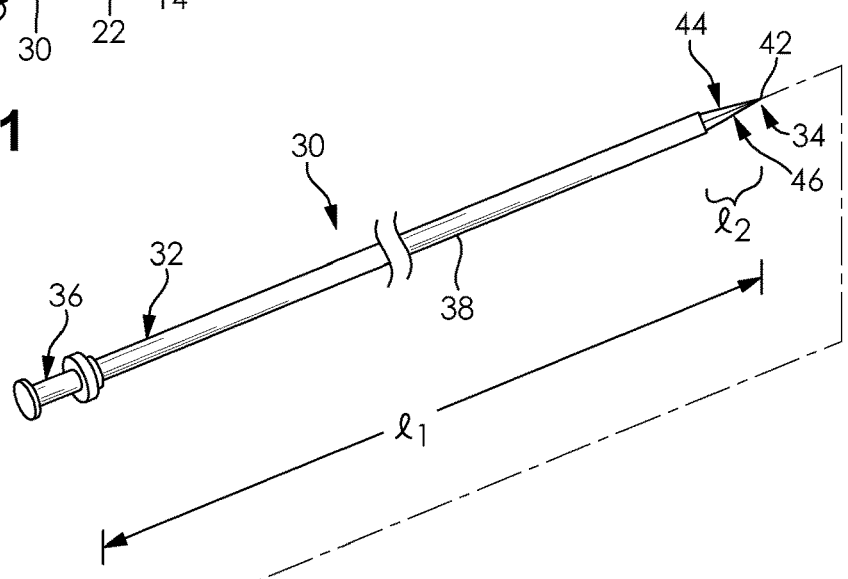
FIG. 2 is an exploded view of the introducer illustrated in FIG. 1.
Figure 2:
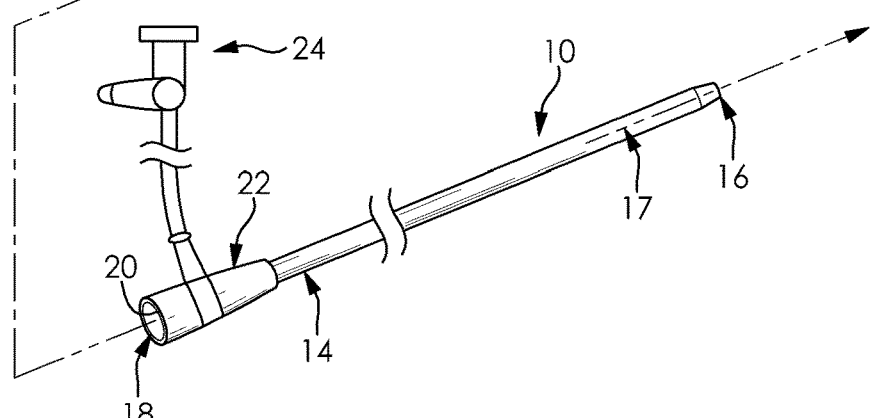
Figure 3:
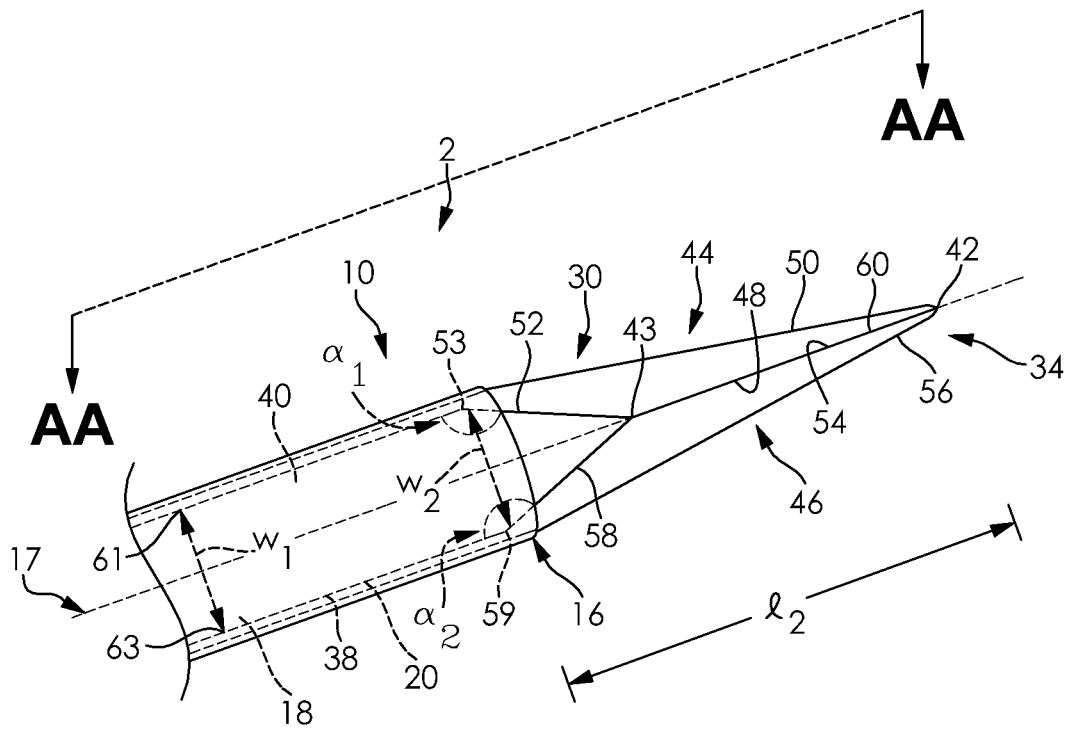
FIG. 3 is a magnified view of area I illustrated in FIG. 1.

The dilator 30 has first and second lengths $l_1$, $l_2$. The first length $l_1$ extends from the proximal end 32 to the distal tip 42, and is best illustrated in FIG. 2. The second length $l_2$ extends from the first and second transition points 53, 59 to the distal tip 42 and is best illustrated in FIGS. 2 and 3. In the illustrated embodiment, the first length $l_1$ is approximately eight times greater than the second length $l_2$. While the first length $l_1$ has been described as approximately eight times greater than the second length $l_2$, the first length of a dilator can be any suitable length relative to the second length of the dilator and skilled artisans will be able to determine suitable first and second lengths for a dilator based on various considerations, including the dimensions of a sheath and dilator included in an introducer, the specific procedure for which an introducer is designed, and the materials that form an introducer. Example lengths for a dilator considered suitable include a first length $l_1$, that is greater than, less than, equal to, or about equal to the second length $l_2$, a first length $l_1$ that is approximately four times greater than a second length $l_2$, a second length $l_2$ that is approximately four times greater than a first length $l_1$, a second length $l_2$ that is approximately eight times greater than a first length $l_1$, and any other length considered suitable for a particular embodiment.

As best illustrated in FIG. 3, the dilator 30 has first and second transition angles $\alpha_1$, $\alpha_2$ that indicate the degree to which the first and second transition portions 52, 58, respectively, taper inwardly, toward the longitudinal axis 17 of the sheath 10 from the main body 38 toward the distal end 34 when the dilator 30 is in the closed configuration. The first and second transition angles $\alpha_1$, $\alpha_2$ are disposed where the main body 38 meets the first and second transition portions 52, 58, respectively. In the illustrated embodiment, the first transition angle $\alpha_1$ is 160° with respect to the main body 38 and the first transition portion 52 and the second transition angle $\alpha_2$ is 160° with respect to the main body 38 and the second transition portion 58. While the first and second transition angles $\alpha_1$, $\alpha_2$ have been described as being 160°, the first and second transition angles can be any suitable angle and skilled artisans will be able to select suitable first and second transition angles based on various considerations, including the dimensions of a sheath and a dilator included in an introducer, and the materials that form an introducer. Example angles considered suitable for each of the first and second transition angles of a dilator when the dilator is in the closed configuration include angles between about 110° and about 180°, angles between about 130° and about 170°, angles between about 155° and about 165°, angles in which the first transition angle $\alpha_1$ is equal to, about equal to, greater than, or less than the second transition angle $\alpha_2$, and any other angle considered suitable for a particular embodiment.

In the illustrated embodiment, when the distal end 34 of the dilator 30 is in the closed configuration, the first and second lateral portions 44, 46 are partially disposed in the lumen 18 of the sheath 10 such that the first and second transition portions 52, 58 and the first and second outer surfaces 50, 56 are partially disposed within the lumen 18 and the first and second inner surfaces 50, 54 are disposed outside the lumen 18. While a particular structural arrangement has been described for the first and second lateral portions 44, 46 when the dilator 30 is in the closed configuration, a dilator can have any suitable structural arrangement when in the closed configuration. Skilled artisans will be able to determine how to suitably position the first and second lateral portions of a dilator with respect to the lumen of a sheath when the distal end of the dilator is in the closed configuration based on various considerations, including the dimensions of a sheath and a dilator of an introducer, the specific procedure for which an introducer is designed, and the materials that form an introducer. Example configurations considered suitable for a dilator when in the closed configuration include configurations in which the entire first lateral portion and the entire second lateral portion of a dilator are entirely disposed within the lumen of a sheath, or outside of a sheath, the first and second transition portions of a dilator and the first and second outer surfaces of the dilator are entirely disposed outside the lumen of a sheath, or inside of a sheath, the entire first lateral portion of a dilator is disposed within the lumen of a sheath and the entire second lateral portion of the dilator is disposed outside the lumen of the sheath, the entire second lateral portion of a dilator is disposed within the lumen of a sheath and the entire first lateral portion of the dilator is disposed outside the lumen of the sheath, and any other configuration considered suitable for a particular embodiment.

In the illustrated embodiment, the dilator 30 has a first width $w_1$ extending continuously across the inner passageway 40 through the longitudinal axis 17 of the sheath 10 (e.g., orthogonally) from a first point 61 disposed on the main body 38 to a second point 63 disposed on the main body 38. The dilator 30 has a second width $w_2$ disposed between the first width $w_1$ and the distal end 34 extending continuously through the longitudinal axis 17 of the sheath 10 (e.g., orthogonally) from the first transition point 53 to the second transition point 59 when the distal end 34 is in the closed configuration. In the illustrated embodiment, the second width $w_2$ is equal to the first width $w_1$ when the dilator 30 is in the closed configuration and the second width $w_2$ is equal to the first width $w_1$ when the dilator 30 is in the open configuration. While the second width $w_2$ has been described as being equal to the first width $w_1$ when the dilator 30 is in the open and closed configurations, the first and second widths of a dilator can be any suitable width and skilled artisans will be able to select a suitable width for a dilator based on various considerations including the materials that form a dilator and the first and second lateral portions of the dilator, and the size and shape of the first and second lateral portions of a dilator. Example widths considered suitable for a dilator include a first width that is greater than, less than, equal to, or about equal to, a second width when the dilator is in the open configuration or closed configuration, and any other width considered suitable for a particular embodiment.

Figure 4:
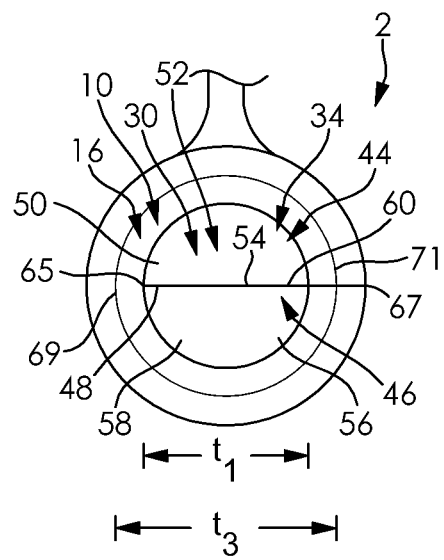
FIG. 4 is a partial end view of the distal end of the introducer illustrated in FIG. 1. The distal end of the dilator is illustrated in the closed configuration.

As illustrated best in FIG. 4, the distal end 34 of the dilator 30 has a first outside diameter $t_1$ when the dilator 30 is in the closed configuration and, as best illustrated in FIG. 5B, the dilator 30 has a second outside diameter $t_2$ when the dilator 30 is in the open configuration. The first outside diameter $t_1$ is measured from a first outer contact point 65 of the first and second lateral portions 44, 46 continuously across the longitudinal axis 17 of the sheath 10 (e.g., orthogonally) to a second outer contact point 67 of the first and second lateral portions 44, 46, when the distal end 34 is in the closed configuration. The first outside diameter $t_1$ of the distal end 34 is greater than the outside diameter of each of the main body 38 and the proximal end 32 and, as a result, the outside diameter of the main body 38 and the proximal end 32 are not visible in FIG. 4. The second outside diameter $t_2$ is measured from a first point on the outer surface of the first lateral portion 44 to a second point on the outer surface of the second lateral portion 46 continuously across the longitudinal axis 17 of the sheath 10 (e.g., orthogonally) when the distal end 34 is in the open configuration. The second outside diameter $t_2$ is greater than the first outside diameter $t_1$. While the first outside diameter $t_1$ of the distal end 34 has been described as greater than the outside diameter of each of the main body 38 and the proximal end 32, a dilator can have a distal end with any suitable outside diameter and skilled artisans will be able to determine a suitable outside diameter for the distal end of a dilator based on various considerations including the specific procedure for which an introducer is designed and the materials that form an introducer. Example outside diameters considered suitable for the distal end of a dilator include outside diameters that are greater than, less than, equal to, or about equal to, the outside diameter of the main body and/or proximal end of the dilator.

The sheath 10 has an outside diameter $t_3$, as illustrated in FIG. 4. The outside diameter $t_3$ is measured from the first sheath point 69 on the distal end 16 continuously across the lumen 18 of the sheath 10 through the longitudinal axis 17 (e.g., orthogonally) to the second sheath point 71 on the distal end 16. In the illustrated embodiment, the outside diameter $t_3$ of the sheath 10 is greater than the first outside diameter $t_1$ of the distal end 34 of the dilator 30 when the distal end 34 of the dilator 30 is in the closed configuration and the outside diameter $t_3$ of the sheath 10 is less than the second outside diameter $t_2$ of the distal end 34 of the dilator 30 when the distal end 34 of the dilator 30 is in the open configuration. While the outside diameter $t_3$ of the sheath 10 has been described as greater than the first outside diameter $t_1$ of the distal end 34 of the dilator 30 when the distal end 34 is in the closed configuration and less than the second outside diameter $t_2$ of the distal end 34 of the dilator 30 when the distal end 34 is in the open configuration, a sheath can have any suitable outside diameter and skilled artisans will be able to determine a suitable outside diameter for a sheath based on various considerations, including the specific procedure for which an introducer is designed and the materials that form an introducer. Example outside diameters considered suitable for a sheath include outside diameters that are greater than, less than, equal to, or about equal to the thickness of the distal end of a dilator when the distal end is in the closed configuration or open configuration.

The distal end 34 of the dilator 30 has a closed configuration, as illustrated in FIGS. 1 through 5A, and an open configuration, as illustrated in FIG. 5B. Proximally-directed movement of the sheath 10 along the longitudinal axis 17 relative to the dilator 30 moves the distal end 34 of the dilator 30 from the closed configuration to the open configuration and results in radially-outward movement of the dilator 30 (e.g., each of the first and second lateral portions 44, 46 described below) relative to the longitudinal axis 17 of the sheath 10. Proximally-directed movement can be characterized in that the distal end 16 of the sheath 10 moves away from the distal end 34 of the dilator 30 and toward the proximal end 32 of the dilator 30. Arrows BB in FIG. 5A indicate proximally-directed movement of the sheath 10. Distally-directed movement of the sheath 10 along the longitudinal axis 17 relative to the dilator 30 moves the distal end 34 of the dilator 30 from the open configuration to the closed configuration and results in radially-inward movement of the dilator 30 (e.g., each of the first and second lateral portions 44, 46) relative to the longitudinal axis 17 of the sheath 10. Distally-directed movement can be characterized in that the distal end 16 of the sheath 10 moves toward the distal end 34 of the dilator 30 and away from the proximal end 32 of the dilator 30. Arrows ZZ in FIG. 5B indicate distally-directed movement of the sheath 10. The handle 36 of the dilator 30 assists with moving the distal end 34 of the dilator 30 between the two configurations. Movement of the distal end 34 of the dilator 30 between its open and closed configurations can be achieved in any suitable manner. For example, movement of the distal end of the dilator 30 between its open and closed configurations can be achieved by applying a proximally-directed or distally-directed force on the dilator 30 (e.g., handle 36) while maintaining the position of the sheath 10, applying a proximally-directed or distally-directed force on the dilator 30 (e.g., handle 36) while also applying a proximally-directed or distally-directed force on the sheath 10, or maintaining the position of the dilator 30 (e.g., handle 36) relative to the sheath 10 while applying a proximally-directed or distally-directed force on the sheath 10. The dilator 30 can be moved axially along the longitudinal axis 17 of the sheath 10 and relative to the sheath 10 (e.g., when the sheath 10 is fixed in place) and can be removed from the sheath 10 by maintaining the position of the sheath 10 and applying a proximally-directed force on the dilator 30. While particular applications of force have been described as achieving movement of the dilator 30 between its open and closed configurations, a dilator can be moved between its open and closed configurations in any suitable manner and using any suitable structure and use of a handle is just one of many ways to generate movement. For example, movement of the distal end of a dilator between the open and closed configurations (e.g., proximal movement of sheath and/or distal movement of dilator) can be achieved by applying a proximally-directed or distally-directed force on a dilator (e.g., handle), applying a rotational force on a dilator (e.g., handle), or by activating a button on the handle of a dilator. For example, in an alternative embodiment, a sheath and a dilator can be at least partially threaded together and the application of a first radial force on the sheath relative to the dilator while maintaining the position of the dilator, the application of a second radial force on the dilator relative to the sheath while maintaining the position of the sheath, or the application of a first radial force on the sheath and the application of a concurrent second radial force opposite the first radial force on the dilator, allows for movement of the distal end of the dilator from one configuration to another. Alternatively, a handle can be omitted from an introducer. It is considered advantageous to move the sheath 10 relative to the dilator 30 to accomplish dilation in place, such that after advancement of the introducer 2 to a point of treatment no additional navigation of the device is necessary to accomplish dilation. This reduces the overall treatment time and the complexity of the procedure being performed.

In the illustrated embodiment, when the distal end 34 of the dilator 30 is in the open configuration, the first and second lateral portions 44, 46 have different shapes than when the distal end 34 of the dilator 30 is in the closed configuration. In the closed configuration, each of the first and second lateral portions 44, 46 of the dilator 30 have a first shape and in the open configuration each of the first and second lateral portions 44, 46 have a second shape. This can be achieved in a number of ways, such as by forming the first and second lateral portions 44, 46 of the dilator 30 of a shape memory material, a shape memory alloy, a shape memory polymer, a deformable material, a deformable memory material, or any other suitable material or combination of materials considered suitable for a particular embodiment. Although the shapes of the first and second lateral portions 44, 46 change when the distal end 34 is moved between the closed configuration and the open configuration, each of the first and second lateral portions 44, 46 is comprised of the same elements in each configuration. The first lateral portion 44 is comprised of the first inner surface 48, the first outer surface 50, and the first transition portion 52 when the distal end 34 is in the open configuration and the closed configuration. The first transition portion 52 defines the first transition angle $\alpha_1$ in the closed configuration and a third transition angle $\alpha_3$ in the open configuration, as described in more detail herein. The second lateral portion 46 is comprised of the second inner surface 54, the second outer surface 56 and the second transition portion 58 in both configurations. The second transition portion 58 defines the second transition angle $\alpha_2$ in the closed configuration and a fourth transition angle $\alpha_4$ in the open configuration. While each of the first and second lateral portions 44, 46 of the dilator 30 have been described as having a first shape in the open configuration and a second shape in the closed configuration, the lateral portions of a dilator can have any suitable shape in the open and closed configurations. Skilled artisans will be able to determine how to shape each of the first and second lateral portions of a dilator when the dilator is in the open configuration or the closed configuration based on various considerations, including the dimensions of a sheath and a dilator included in an introducer, the specific procedure for which an introducer is designed, and the materials that form an introducer. Example shapes considered suitable for the lateral portions of a dilator include each of first and second lateral portions of a dilator having the same shape in the open and closed configurations, the first lateral portion of a dilator having a first shape in the closed configuration and the second lateral portion of the dilator having a second shape different than the first shape in the closed configuration, the first lateral portion of a dilator having a first shape in the open configuration and the second lateral portion of the dilator having a second shape different than the first shape in the open configuration, combinations of the configurations described herein, and any other configuration considered suitable for a particular embodiment.

In the illustrated embodiment, each of the first and second lateral portions 44, 46 has a rounded tetragonal cross-sectional shape when the distal end 34 of the dilator 30 is the open configuration and the closed configuration. Cross-sectional shapes of the first and second lateral portions 44, 46 are illustrated in FIGS. 5A and 5B. The first inner surface 48, the first outer surface 50, the first transition portion 52, and the first main body side 55 define the cross-sectional shape of the first lateral portion 44. When the distal end 34 of the dilator 30 is in the closed configuration, the first main body side 55 is adjacent the first outer surface 50 and the first transition portion 52, and the first inner surface 48 is adjacent the first transition portion 52 and the first outer surface 50. When the distal end 34 of the dilator 30 is in the open configuration, the first main body side 55 is adjacent the first transition portion 52 and the first inner surface 48, and the first inner surface 48 is adjacent the first main body side 55 and the first outer surface 50. The second inner surface 54, the second outer surface 56, the second transition portion 58, and the second main body side 57 define the cross-sectional shape of the second lateral portion 46. When the distal end 34 of the dilator 30 is in the closed configuration, the second main body side 57 is adjacent the second outer surface 56 and the second transition portion 58, and the second inner surface 54 is adjacent the second transition portion 58 and the second outer surface 56. When the distal end 34 of the dilator 30 is in the open configuration, the second main body side 57 is adjacent the second transition portion 58 and the second inner surface 54, and the second inner surface 54 is adjacent the second main body side 57 and the second outer surface 56. The first and second main body sides 55, 57 are approximately opposite one another with respect to the longitudinal axis 17 of the sheath 10 and are disposed on the most distal portion of the main body 38 that meets the first and second lateral portions 44, 46. Each of the first and second main body sides 55, 57 extends from an outer surface of the dilator 30 to an inner surface of the dilator 30 that defines inner passageway 40.

As illustrated, the first and second lateral portions 44, 46 have the same cross-sectional shapes that are oriented differently when the distal end 34 of the dilator 30 is in the closed configuration and the open configuration. However, alternative embodiments can include first and second lateral sides that have any suitable cross-sectional shape and skilled artisans will be able to determine a suitable cross-sectional shape for a lateral portion of a dilator based on various considerations, including the dimensions of a sheath and a dilator of an introducer, the specific procedure for which an introducer is designed, and the materials that form an introducer. Example cross-sectional shapes for the first and second lateral portions of a dilator include a first lateral portion that has a cross-sectional shape that is different than the cross-sectional shape of a second lateral portion when the dilator is in the open configuration and/or closed configuration, a first lateral portion that has a cross-sectional shape that is the same as the second lateral portion when the dilator is in the open configuration and/or closed configuration, a first lateral portion and/or second lateral portion that has a rounded, rectangular cross-sectional shape, a first lateral portion and/or second lateral portion that has a triangular cross-sectional shape, a first lateral portion and/or second lateral portion that has a rounded tetragonal cross-sectional shape, a first lateral portion and/or second lateral portion that has an elliptical cross-sectional shape, and any other cross-sectional shape considered suitable for a particular embodiment.

In the open configuration, as shown in FIG. 5B, the dilator 30 has third and fourth transition angles $\alpha_3$, $\alpha_4$ that indicate the degree to which the first and second transition portions 52, 58, respectively, are ramped outwardly away from the longitudinal axis 17 of the sheath 10 from the main body 38 toward the distal end 34. In the illustrated embodiment, the third transition angles $\alpha_3$ is 160° with respect to the main body 38 and the first transition portion 52 and the fourth transition angle $\alpha_4$ is 160° with respect to the main body 38 and the second transition portion 58. While the third and fourth transition angles $\alpha_3$, $\alpha_4$ have been described as being 160°, the third and fourth transition angles of a dilator can be any suitable angle and skilled artisans will be able to determine suitable third and fourth transition angles based on various considerations, including the dimensions of a sheath and a dilator of an introducer, and the materials that form an introducer. Example angles considered suitable for the third and fourth transition angles of a dilator when the dilator is in the open configuration include angles between about 110° and about 180°, angles between about 130° and about 170°, angles between about 155° and about 165°, angles in which the third transition angle is greater than, less than, equal to, or about equal to, a fourth transition angle, and any other angle considered suitable for a particular embodiment.

In contrast to when the distal end 34 of the dilator 30 is in the closed configuration, the first inner surface 48 and second inner surface 54 are spaced from each other with respect to the longitudinal axis 17 of the sheath 10 when the distal end 34 of the dilator 30 is in the open configuration. In the closed configuration, the first inner surface 48 and second inner surface 54 contact one another and in the open configuration the first inner surface 48 and second inner surface 54 are separated and not contacting one another. While particular configurations of a dilator have been described, a dilator can have any suitable configuration in an open configuration and skilled artisans can select a suitable configuration for a dilator in the open configuration based on various considerations, such as the structure of the bodily passage intended to be treated. For example, in an alternative embodiment, the first inner surface and second inner surface of a dilator can intermittently contact one another when the distal end of the dilator is in the open configuration. In another alternative embodiment, the first and second inner surfaces of a dilator can be spaced from each other with respect to an axis other than the longitudinal axis when the distal end of the dilator is in the open configuration.

The first and second inner surfaces 48, 54 are parallel to the longitudinal axis 17 of the sheath 10 when the distal end 34 of the dilator 30 is in the closed and open configurations. In the illustrated embodiment, the first inner surface 48 is parallel to the longitudinal axis 17 of the sheath 10 and the second inner surface 54. Though the figures illustrate the first and second inner surfaces 48, 54 as parallel to the longitudinal axis 17 of the sheath 10, one or both of the first and second inner surfaces of a dilator can alternatively be angled with respect to the longitudinal axis of a sheath in either the open or closed configurations. Skilled artisans will be able to determine how to suitably orient the first and second inner surfaces of a dilator with respect to the longitudinal axis of a sheath based on various considerations, including the dimensions of a sheath and a dilator of an introducer, the specific procedure for which an introducer is designed, and the materials that form an introducer. For example, in an alternative embodiment, the first inner surface of a dilator can be parallel to the longitudinal axis of a sheath and the second inner surface of the dilator can be disposed on a plane that is obtusely angled with respect to the longitudinal axis of the sheath in the open and/or closed configuration. In another alternative embodiment, each of the first and second inner surfaces of a dilator can be disposed on planes that are acutely or obtusely angled with respect to the longitudinal axis of a sheath in the open and/or closed configuration. In another alternative embodiment, the first inner surface of a dilator can be disposed on a first plane that is angled to a particular degree with respect to the longitudinal axis of a sheath while the second inner surface of the dilator can be disposed on a second plane that is angled to a different particular degree than the first plane containing the first inner surface when the dilator is in the open and/or closed configuration.

Figure 6:
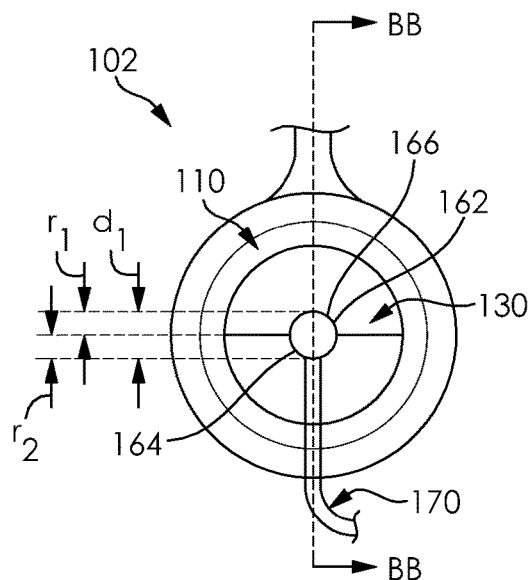
FIG. 6 is a partial end view of the distal end of another embodiment of an introducer. The distal end of the dilator is illustrated in the closed configuration.
Figure 7:
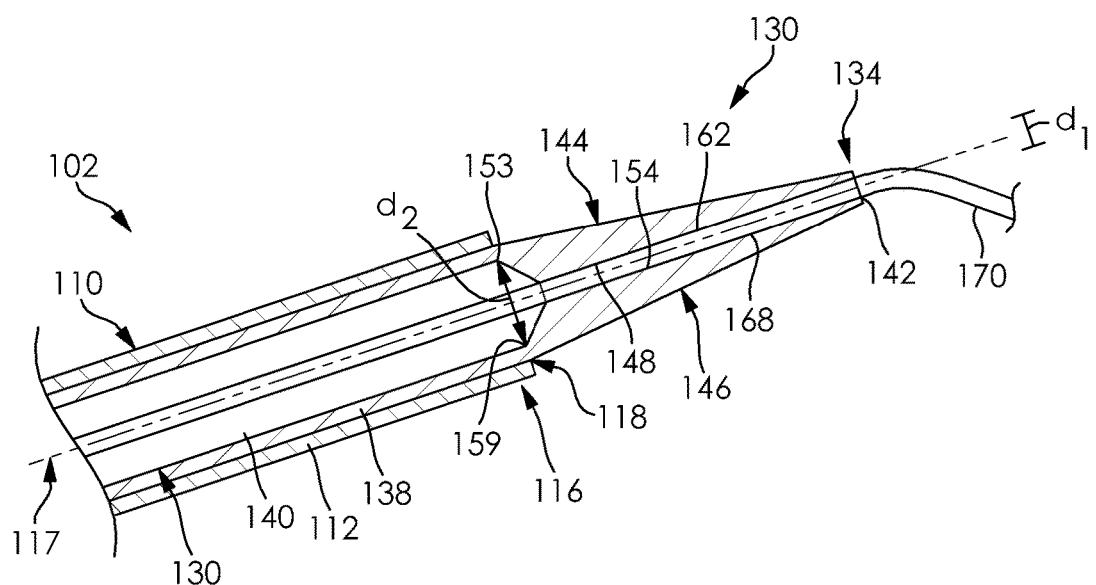
FIG. 7 is a partial cross-sectional view of the distal end of the introducer illustrated in FIG. 6 taken along line BB-BB. The distal end of the dilator is illustrated in the closed configuration.

FIGS. 6 and 7 illustrate another example introducer 102. The introducer 102 illustrated in FIGS. 6 and 7 is similar to the introducer 2 illustrated in FIGS. 1 through 5B and described above, except as detailed below. Thus, the introducer 102 comprises a sheath 110 and a dilator 130. The sheath 110 has a main body 112, a distal end 116, a lumen 118, and a longitudinal axis 117. The dilator 130 is disposed within the lumen 118 and has a distal end 134, a main body 138, an inner passageway 140, a distal tip 142, a first lateral portion 144, and a second lateral portion 146.

In the embodiment illustrated in FIGS. 6 and 7, the first lateral portion 144 defines a first notch 162 and the second lateral portion 146 defines a second notch 164. The first notch 162 extends from the distal tip 142 along the first inner surface 148 to the first transition point 153 and the second notch 164 extends from the distal tip 142 along the second inner surface 154 to the second transition point 159. The first and second notches 162, 164 cooperatively define an opening 166 on the distal end 134 of the dilator 130 and a channel 168 when the distal end 134 is in the closed configuration. The channel 168 is in communication with the inner passageway 140 and extends from the distal tip 142 to the first and second transition points 153, 159 of the first and second transition portions 152, 158.

Each of the first and second notches 162, 164 is semicircular in shape and configured such that when the distal end 136 of the dilator 130 is in the closed configuration and the first and second inner surfaces 148, 154 are in contact with one another, the first and second notches 162, 164 mate and cooperatively define the opening 166 on the distal end 136. While each of the first and second notches 162, 164 has been described as semicircular in shape, a notch included on a dilator can have any suitable shape and skilled artisans will be able to determine a suitable shape for a notch based on various considerations, including the dimensions of a sheath and a dilator of an introducer, and the materials that form an introducer. Example shapes considered suitable for a notch included on a dilator include notches that are semi-elliptical and mate to cooperatively define an elliptical opening on the distal end of a dilator, notches that are rectangular and mate to cooperatively define a rectangular opening on the distal end of a dilator, a first notch that has a first shape (e.g., rectangular, semi-circular, semi-elliptical) and a second notch that has a second shape (e.g., rectangular, semi-circular, semi-elliptical) that is different that the first shape, a first notch that has a first shape and a second notch that has a second shape that is the same as the first shape, and any other shape considered suitable for a particular embodiment.

As illustrated in FIG. 6, the first notch 162 has a first radius $r_1$ of curvature and the second notch 164 has a second radius $r_2$ of curvature. As shown in FIG. 7, the channel 168 has a first diameter $d_1$ at the distal tip 142 and a second diameters $d_2$ at the first and second transition points 153, 159. The first and second radii $r_1$, $r_2$ are measured at the distal tip 142 and are equal to one another in the illustrated embodiment. While the first and second radii $r_1$, $r_2$ have been described as being equal to one another, the first and second radii of a dilator can have any suitable radius and skilled artisans will be able to determine suitable radius for the first and second radii $r_1$, $r_2$ of a dilator based on various considerations, including the dimensions of a sheath and a dilator of an introducer. For example, in an alternative embodiment, the first radius of curvature $r_1$ can be greater than, less than, equal to, or about equal to the second radius of curvature $r_2$. The first diameter $d_1$ of the channel 168 is defined at the distal tip 142 and is equal to the combined first and second radii $r_1$, $r_2$ of the respective first and second notches 162, 164. In the illustrated embodiment, the second diameter $d_2$ is greater than the first diameter $d_1$. Thus, the channel 166 tapers distally from the first and second transition points 153, 159 to the distal tip 142. While the second diameter $d_2$ has been described as greater than the first diameter $d_1$, the second diameter of a dilator can be any suitable diameter relative to the first diameter of the dilator and skilled artisans will be able to determine suitable first and second diameters based on various considerations, including the dimensions of a sheath and a dilator of an introducer. For example, a second diameter can be greater than, less than, equal to, or equal to about the first diameter.

As illustrated, a guidewire 170 is disposed within the inner passageway 140 of the dilator 130. The guidewire 170 is threaded through the dilator 130, along the channel 168, and is passed through the opening 166 defined by the first and second notches 162, 164. During use, the guidewire 170 assists with aligning a puncture site with the introducer 102. A skilled artisan will be able to determine whether the use of a guidewire is appropriate for a particular embodiment based on various considerations, including the specific procedure for which an introducer is designed. For example, a guidewire can be included, or omitted, from any of the embodiments described herein.

Figure 8A:
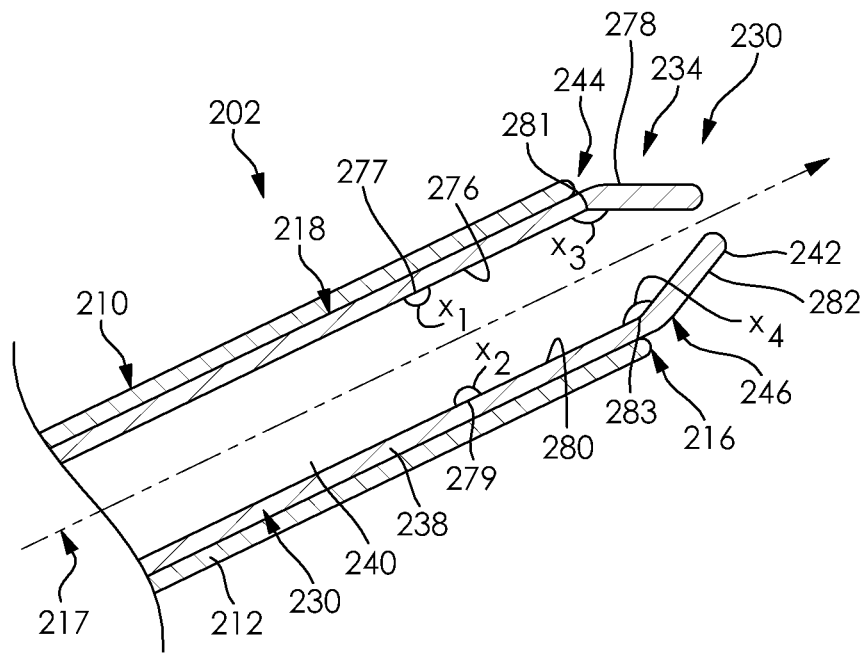
FIG. 8A is a partial cross-sectional view of the distal end of another embodiment of an introducer taken along a plane that is perpendicular to the longitudinal axis of the sheath. The distal end of the dilator is illustrated in the closed configuration.
Figure 8B:
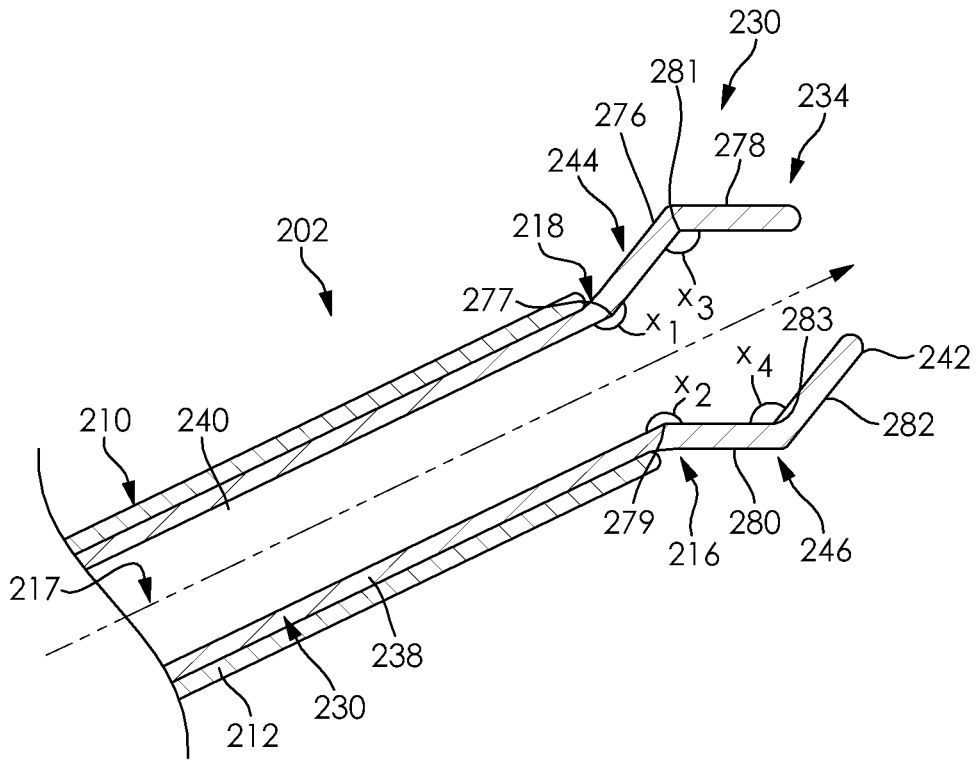
FIG. 8B is a view of the distal end of the introducer illustrated in FIG. 8A in which the distal end of the dilator is illustrated in the open configuration.

FIGS. 8A and 8B illustrate another example introducer 202. The introducer 202 illustrated in FIGS. 8A and 8B is similar to the introducer 2 illustrated in FIGS. 1 through 5B and described above, except as detailed below. Thus, the introducer 202 comprises a sheath 210 and a dilator 230. The sheath 210 has a main body 212, a distal end 216, a lumen 218, and a longitudinal axis 217. The dilator 230 is disposed within the lumen 218 and has a distal end 234, a main body 238, an inner passageway 240, a distal tip 242, a first lateral portion 244, and a second lateral portion 246.

In the embodiment illustrated in FIGS. 8A and 8B, the first lateral portion 244 comprises a first upper segment 276 and a second upper segment 278. The first upper segment 276 is adjacent the second upper segment 278 and the main body 238. The second lateral portion 242 comprises a first lower segment 280 and a second lower segment 282. The first lower segment 280 is adjacent the second lower segment 282 and the main body 238. The illustrated embodiment also comprises a first bend 277, a second bend 279, a third bend 281, and a fourth bend 283. The first bend 277 has a first interior angle $\chi_1$ and is disposed at the point at which the first upper segment 276 adjoins the main body 238. The second bend 279 has a second interior angle $\chi_2$ and is disposed at the point at which the first lower segment 280 adjoins the main body 238. The third bend 281 has a third interior angle $\chi_3$ and is disposed at the point at which the first upper segment 276 adjoins the second upper segment 278. The fourth bend 283 has a fourth interior angle $\chi_4$ and is disposed at the point at which the first lower segment 280 adjoins the second lower segment 282.

In the illustrated embodiment, the first and second bends 277, 279 are approximately opposite one another with respect to the longitudinal axis 217 of the sheath 210 and the third and fourth bends 281, 283 are approximately opposite one another with respect to the longitudinal axis 217 of the sheath 210. While the first and second bends 277, 279 have been described as being approximately opposite one another with respect to the longitudinal axis 217 of the sheath 210 and the third and fourth bends 281, 283 have been described as being approximately opposite one another with respect to the longitudinal axis 217 of the sheath 210, a dilator can include any suitable number of bends and a first bend can be positioned at any suitable location relative to a second bend and a third bend can be positioned at any suitable location relative to a fourth bend. Skilled artisans will be able to determine whether to include one or more bends on a dilator and how best to dispose them on a dilator based on various considerations, including the material or materials from which the dilator is formed. Example locations considered suitable to position one or more bends on a dilator include positioning each of the first and second bends of a dilator a first distance from the distal end of the dilator and the third and fourth bends a second distance from the distal end of the dilator that is equal to, about equal to, less than, or greater than the first distance, positioning the first and second bends such that they are staggered in relation to one another with respect to the longitudinal axis of a sheath (e.g., not opposite), and any other position considered suitable for a particular embodiment. Example number of bends considered suitable to include on a dilator include zero, one, at least one, two, three, four, five, six, seven, and any other number considered suitable for a particular embodiment. For example, a dilator can define first and third bends and omit second and/or fourth bends, or vice versa.

The second upper segment 278 has a rounded tetragonal cross-sectional shape and has the same cross-sectional shape as the second lower segment 282. The first upper segment 276 has a rectangular cross-sectional shape and has the same cross-sectional shape as the first lower segment 280. While the second upper segment 278 and second lower segment 282 have been described as having a rounded tetragonal cross-sectional shape and the first upper segment 276 and first lower segment 280 have been described as having a rectangular cross-sectional shape, the segments of a dilator can have any suitable cross-sectional shape. Skilled artisans will be able to determine suitable cross-sectional shapes and sizes for a segment included on a dilator based on various considerations, including the dimensions of a sheath and a dilator of an introducer, and the materials that form an introducer. Example cross-sectional shapes considered suitable for a segment of a dilator include triangular cross-sectional shapes, first and second upper segments of a dilator having a rounded rectangular cross-sectional shape and first and second lower segments having an elliptical cross-sectional shape, a first upper segment having a triangular cross-sectional shape, a second upper segment having an elliptical cross-sectional shape, a first lower segment having a rounded rectangular cross-sectional shape, a second lower segment having a square cross-sectional shape, combinations of the configurations described herein, and any other configuration considered suitable for a particular embodiment. The cross-sectional shapes and sizes of the segments 276, 278, 280, 282 illustrated in FIGS. 8A and 8B are illustrative in nature and are provided to enable a skilled artisan to make and use the introducer 202 and are not designed to limit the scope of the claims in any manner.

FIG. 8A illustrates the first upper segment 276 on a first plane and the first lower segment 280 on a second plane when the distal end 234 of the dilator 230 is in the closed configuration. Each of the two planes is substantially parallel (e.g., within 0.5 degrees of parallel, within 1 degree of parallel, within 10 degrees of parallel) to the longitudinal axis 217 of the sheath 210 resulting in the first upper segment 276 being parallel to each of the first lower segment 280 and the longitudinal axis 217 of the sheath 10. While the first upper segment 276 has been described as being positioned on a first plane that is parallel to the longitudinal axis 217 of the sheath 210 and the first lower segment 280 has been described as being positioned on a second plane that is parallel to the longitudinal axis 217 of the sheath 210 when the distal end 234 of the dilator 230 is in the closed configuration, a first upper segment and first lower segment can be positioned on any suitable plane relative to the longitudinal axis of a sheath when a dilator is in the closed configuration. Skilled artisans will be able to determine suitable orientations with respect to the longitudinal axis for each of the segments based on various considerations, including the dimensions of a sheath and a dilator of an introducer, and the materials that form a sheath and/or dilator of an introducer. Example positions considered suitable for the segments included on a dilator include a first lower segment that is parallel to the longitudinal axis of a sheath when the distal end is in the closed configuration while a first upper segment is located on a plane that is angled toward (e.g., not parallel to) the longitudinal axis of the sheath, a first upper segment and/or a first lower segment that are disposed on planes that are angled toward (e.g., not parallel to) the longitudinal axis of a sheath when the distal end is in the closed configuration, a first upper segment that is disposed on a plane that is angled differently with respect to the longitudinal axis of a sheath than the plane on which a first lower segment is disposed, combinations of the configurations described herein, and any other position considered suitable for a particular embodiment.

In the illustrated embodiment, the third interior angle $\chi_3$ is 150° with respect to the first upper segment 276 and the second upper segment 278 when the distal end 234 of the dilator 230 is in the closed configuration and the fourth interior angle $\chi_4$ is 150° with respect to the first lower segment 280 and the second lower segment 282 when the distal end 234 of the dilator 230 is in the closed configuration. However, the third and fourth interior angles $\chi_3$, $\chi_4$, can have any angular measurement and skilled artisans will be able to determine suitable third and fourth interior angles based on various considerations, including the procedure for which an introducer is intended to be used. Example angles considered suitable for third and fourth interior angles when a dilator is in the closed configuration include angles between about 90° and about 180°, angles between about 110° and about 170°, angles between about 120° and about 160°, and any other angle considered suitable for a particular embodiment.

The second upper segment 278 and the second lower segment 282 are spaced in relation to one another when the distal end 234 of the dilator 230 is in the closed configuration, as illustrated in FIG. 8A. Therefore, depending on the procedure being accomplished, a guidewire or other device may be passed through the inner passageway 240 and between the second upper segment 278 and the second lower segment 282 when the distal end 234 is in the closed configuration. Alternatively, a second upper segment and a second lower segment of a dilator can directly contact one another such that a guidewire or other device cannot pass between the segments when the distal end is in the closed configuration. Skilled artisans will be able to determine how best to position a second upper segment and a second lower segment of a dilator when the distal end of the dilator is in the closed configuration based on various considerations, including the procedure for which an introducer is intended to be used. For example, a second upper segment and a second lower segment of a dilator can contact one another in a manner such that a guidewire or other device may be passed between the segments when the distal end of the dilator is in the closed configuration.

The second upper segment 278 and second lower segment 282 are partially disposed outside the lumen 218 of the sheath 210 when the distal end 234 is in the closed configuration. In contrast, the first upper segment 276 and first lower segment 280 are entirely disposed within the lumen 218 of the sheath 210 when the distal end 234 is in the closed configuration. While a particular configuration of the dilator 230 relative to the sheath 210 has been described, a dilator of an introducer can be positioned in any suitable manner relative to a sheath. Skilled artisans will be able to determine how to suitably position the segments of a dilator in relation to the lumen of a sheath when the distal end of the dilator is in the closed configuration based on various considerations, including the dimensions of a sheath and a dilator and the procedure for which an introducer is intended to be used. Example configurations considered suitable for a dilator relative to a sheath when the dilator is in the closed configuration include configurations in which each of the segments of a dilator is entirely disposed within the lumen of a sheath, each of the segments of a dilator is entirely disposed outside the lumen of a sheath, the second upper segment of a dilator is disposed outside the lumen of a sheath while the remaining segments of the dilator are disposed entirely within the lumen of the sheath, combinations of the configurations described herein, and any other configuration considered suitable for a particular embodiment (e.g., any of the segments of a dilator may be disposed within or outside the lumen of a sheath when the distal end of the dilator is in the closed configuration).

In the illustrated embodiment, the first and second bends 277, 279 change between the open and closed configurations and the third and fourth bends 281, 283 are fixed between the open and closed configurations. This can be achieved in a number of ways, such as by forming the first and second lateral portions 244, 246, or portions of the first and second lateral portions 244, 246 (e.g., first upper segment 276 and/or first lower segment 280), of the dilator 230 of a shape memory alloy, a shape memory material, a shape memory polymer, a deformable material, a deformable memory material, or another material or combination of materials considered suitable for a particular embodiment. Although the particular angles of the first and second bends 277, 279 change when the distal end 234 of the dilator 230 is moved between the closed configuration and the open configuration, the bends continue to define first and second interior angles $\chi_1$, $\chi_2$, respectively. Alternative embodiments can include a dilator in which the first and second bends of the dilator are fixed between the open and closed configurations and the third and fourth bends of the dilator are fixed between the open and closed configurations or in which the first and second bends of the dilator are fixed between the open and closed configurations and the third and fourth bends of the dilator change between the open and closed configurations.

In FIG. 8B, the first interior angle $\chi_1$ is 210° with respect to the main body 238, and the first upper segment 276, the second interior angle $\chi_2$ is 210° with respect to the main body 238 and the first lower segment 280, the third interior angle $\chi_3$ is 150° with respect to the first upper segment 276 and second upper segment 278, and the fourth interior angle $\chi_4$ is 150° with respect to the first lower segment 280 and second lower segment 282 when the distal end 234 of the dilator 230 is in the open configuration. While specific angles have been described for the first, second, third, and fourth interior angles $\chi_1$, $\chi_2$, $\chi_3$, $\chi_4$, a dilator can define any suitable interior angle and skilled artisans will be able to determine suitable interior angles based on various considerations, including the material or materials from which the distal end of a dilator is formed and the sizes and desired shapes of the segments. Example interior angles considered suitable for a dilator when the dilator is in the open configuration include angles in which each of the third and fourth interior angles is between about 90° and about 180°, each of the third and fourth interior angles is between about 110° and about 170°, each of the third and fourth interior angles is between about 120° and about 160°, each of the first and second interior angles is between about 150° and about 270°, each of the first and second interior angles is between about 180° and about 240°, each of the first and second interior angles is between about 200° and about 220°, angles in which the first and second interior angles are different and/or each of the third and fourth interior angles are different, and any other angle considered suitable for a particular embodiment.

Figure 9A:
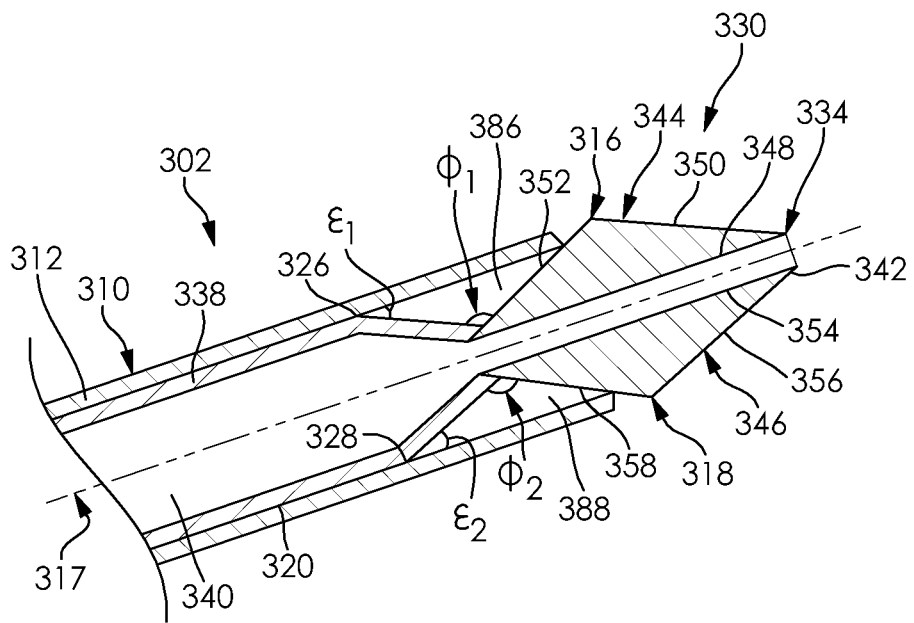
FIG. 9A is a partial cross-sectional view of the distal end of another embodiment of an introducer taken along a plane that is perpendicular to the longitudinal axis of the sheath. The distal end of the dilator is illustrated in the closed configuration.
Figure 9B:
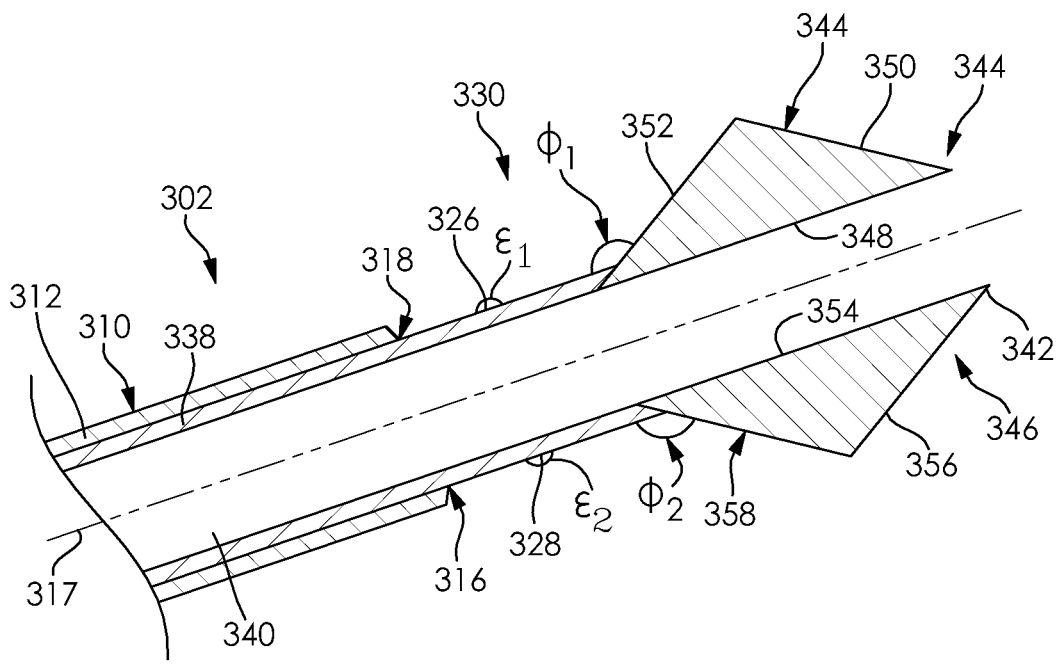
FIG. 9B is a view of the distal end of the introducer illustrated in FIG. 9A in which the distal end of the dilator is illustrated in the open configuration.

FIGS. 9A and 9B illustrate another example introducer 302. The example introducer 302 illustrated in FIGS. 9A and 9B is similar to introducer 2 illustrated in FIGS. 1 through 5B and described above, except as detailed below. Thus, the introducer 302 comprises a sheath 310 and a dilator 330. The sheath 310 has a main body 312, a distal end 316, a lumen 318, and a longitudinal axis 317. The dilator 330 is disposed within the lumen 318 and has a distal end 334, a main body 338, an inner passageway 340, a distal tip 342, a first lateral portion 344, and a second lateral portion 346.

In the embodiment illustrated in FIGS. 9A and 9B, the dilator 330 defines an upper bend 326 and a lower bend 328. The upper bend 326 is disposed between the proximal end 332 and the distal end 334 of the main body 338 and defines an upper bend angle $\varepsilon_1$. The lower bend 328 is disposed between the proximal end 332 and distal end 334 of the main body 338 and defines a lower bend angle $\varepsilon_2$.

The upper and lower bends 326, 328 are approximately opposite one another relative to the longitudinal axis 317 of the sheath 310 when the distal end 334 is in the closed configuration and biased the dilator 330 to the open configuration. While a particular configuration has been described with respect to the upper and lower bends, a dilator can include any suitable configuration of bends and skilled artisans will be able to determine whether to include one or more upper and lower bends and how best to dispose the them on a dilator based on various considerations, including the material or materials from which the distal end of a dilator is formed. Example configurations considered suitable for an upper bend and a lower bend include configurations in which the upper bend and/or lower bend are/is disposed a first distance from the distal end of a dilator and the proximal end of the first lateral portion and/or second lateral portion are/is disposed a second distance from the distal end of the dilator that are/is equal to, about equal to, greater than, or less than the first distance, upper and lower bends that are staggered in relation to one another with respect to the longitudinal axis of a sheath, a dilator that defines an upper bend but not a lower bend, a dilator that defines a lower bend but not an upper bend, combinations of the configurations described herein, and any other configuration considered suitable for a particular embodiment.

The first and second lateral portions 344, 346 have a substantially triangular cross-sectional shape. The first lateral portion 344 is comprised of three sides, which include the first inner surface 348, the first outer surface 350, and the first transition portion 352. Each side of the first lateral portion 344 is adjacent the two other sides. The second lateral portion 346 is comprised of three sides, which include the second inner surface 354, the second outer surface 356, and the second transition portion 358. Each side of the second lateral portion 346 is adjacent the two other sides. While the first and second lateral portions 344, 346 have been described as having a particular structural arrangement, the lateral portions of a dilator can have any suitable structural arrangement and skilled artisans will be able to determine suitable cross-sectional shapes for each of the first and second lateral portions of a dilator based on various considerations, including the dimensions of a sheath and a dilator of an introducer, and the materials that form an introducer. Example structural arrangements for the first and second lateral portions of a dilator include first and second lateral portions that have any suitable number of sides that cooperatively define their respective cross-sectional shapes, each of the first and second lateral portions having a rectangular cross-sectional shape, each of the first and second lateral portions having an elliptical cross-sectional shape, each of the first and second lateral portions having a circular cross-sectional shape, combinations of the shapes described herein, and any other configuration considered suitable for a particular embodiment.

Though the figures illustrate the first and second lateral portions 344, 346 having the same cross-sectional shapes, a first lateral portion of a dilator may have a different cross-sectional shape than a second lateral portion of the dilator. Skilled artisan will be able to determine whether each of the first and second lateral portions of a dilator should have the same cross-sectional shape based on various considerations, including the procedure for which an introducer is intended to be used. Example configurations considered suitable between first and second lateral portions include a first lateral portion that has a rectangular cross-sectional shape and a second lateral portion that has a triangular cross-sectional shape, a first lateral portion that has a circular cross-sectional shape and a second lateral portion that has an elliptical cross-sectional shape, combinations of the configurations described herein, and any other configuration or cross-sectional shape considered suitable for a particular embodiment.

Each of the first and second transition portions 352, 358 extends from the main body 338 toward the distal end 334 and is ramped outwardly with respect to the longitudinal axis 317 of the sheath 310. The first and second transition angles $\phi_1$, $\phi_2$ indicate the degrees to which the first and second transition portions 352, 358, respectively, are ramped outwardly with respect to the main body 338. In the illustrated embodiment, each of the first and second transition angles $\phi_1$, $\phi_2$ is 140° with respect to the main body 338 and the respective transition portions 352, 358 when the dilator 330 is in the closed configuration. The first and second transition angles $\phi_1$, $\phi_2$ may have any suitable angle, though and skilled artisans will be able to determine suitable first and second transition angles for a dilator based on various considerations, including the dimensions of a sheath and a dilator of an introducer. Example angles considered suitable for the first and second transition angles of a dilator when the dilator is in the open configuration or closed configuration include angles between about 90° and about 180°, angles between about 120° and about 150°, angles between about 135° and about 145°, and any other angle considered suitable for a particular embodiment.

As illustrated, each of the upper and lower bend angles $\epsilon_1$, $\epsilon_2$ is 30° with respect to the main body 338 and the sheath 310 when the distal end 334 is in the closed configuration. While particular angles have been described for the upper and lower bend angles $\epsilon_1$, $\epsilon_2$ when the dilator 330 is in the closed configuration, the upper and lower bend angles of a dilator can be defined at any suitable angle and skilled artisans will be able to determine suitable upper and lower bend angles for a dilator based on various considerations, including the dimensions of a sheath and a dilator of an introducer. Example angles considered suitable for the upper and lower bend angles of a dilator include angles between about 0° and about 90°, angles between about 10° and about 60°, angles between about 20° and about 40°, and any other angle considered suitable for a particular embodiment. The figures illustrate the upper bend angle $\epsilon_1$ as equal to the lower bend angle $\epsilon_2$ when the distal end 334 is in the closed configuration. However, other configurations are considered suitable and skilled artisans will be able to determine whether to identically angle the upper and lower bend angles $\epsilon_1$, $\epsilon_2$ based on various considerations, including the materials that form a dilator. For example, an alternative embodiment can include upper bend angle $\epsilon_1$ that is greater than, less than, equal to, or about equal to the lower bend angle $\epsilon_2$.

FIG. 9A best illustrates the first inner surface 348 being spaced in relation to the second inner surface 354 with respect to the longitudinal axis 317 when the distal end 336 is in the closed position. However, other structural arrangements are considered suitable for a dilator in the closed configuration and skilled artisans will be able to determine whether it is suitable for the first and second inner surfaces to contact one another and how the first and second inner surfaces should contact one another when the distal end is in the closed configuration based on various considerations, including the intended use of an introducer. For example, an introducer can include a dilator that has a first inner surface and a second inner surface that intermittently contact one another when the distal end is in the closed configuration, a first inner surface and a second inner surface that continuously contact another when the distal end is in the closed configuration forming an interface disposed along the longitudinal axis, and any other configuration considered suitable for a particular embodiment.

The sheath 310 and the dilator 330 define an upper gap 386 and a lower gap 388 when the dilator 330 is in the closed configuration. The gaps 386, 388 are empty spaces defined by the sheath 310 and dilator 330. A portion of the main body 338, the first transition portion 352, and the inner surface 320 of the sheath 310 define the upper gap 386. A portion of the main body 338, the second transition portion 358, and the inner surface 320 define the lower gap 388. In the illustrated embodiment, the dilator 330 and sheath 310 define each of the upper and lower gaps 386, 388 when the distal end 334 is in the closed configuration and do not define either gap when the distal end 334 is in the open configuration. However, other configurations are considered suitable. For example, a sheath and dilator can define upper and lower gaps only when the distal end of the dilator is in the open configuration, can define only one of the upper and lower gaps when the distal end of the dilator is in the closed configuration, can define only one of the upper and lower gaps when the distal end of the dilator is in the open configuration, and any other configuration considered suitable for a particular embodiment. In an alternative embodiment, a dilator and a sheath can omit the inclusion of an upper gap and/or a lower gap in either configuration.

For the purposes of this application, a cross-sectional outline is defined as a set of edges disposed on one or more elements that indicate the define the shape of an empty area after a cross-section is taken of the empty area. For example, the upper gap 386 is outlined by a portion of the main body 338, the first transition portion 352, and the inner surface 320, and has a triangular cross-sectional outline. The lower gap 388 is outlined by a portion of the main body 338, the second transition portion 358, and the inner surface 320, and has a triangular cross-sectional outline. While particular cross-sectional outlines have been described, each of the upper and lower gaps of a dilator can have any suitable cross-sectional outline and skilled artisans will be able to determine how to shape the upper and lower gaps of a dilator based on various considerations, including the procedure intended to be completed. For example, the upper gap and/or lower gap can have a cross-sectional outline that is a square, a rectangle, a circle, a rhombus, a trapezoid, or any other shape considered suitable for a particular embodiment.

In the illustrated embodiment, when the distal end 334 of the dilator 330 is in the open configuration, the upper and lower bends 326, 328 have different values than when the distal end 334 of the dilator 330 is in the closed configuration. This can be achieved in a number of ways, such as through forming the main body 338 of a shape memory material, a shape memory alloy, a shape memory polymer, a deformable material, a deformable memory material, or another material or combination of materials considered suitable for a particular embodiment. Although the angles of the upper and lower bends 326, 328 change when the distal end 334 is moved from the closed configuration to the open configuration, the bends continue to define upper and lower bend angles $\varepsilon_1$, $\varepsilon_2$, respectively. A skilled artisan will be able to determine a suitable means to ensure the upper and lower bends 326, 328 are angled differently in the two configurations based on various considerations, including the dimensions of a sheath and a dilator, the specific procedure for which an introducer is designed, and the materials that form an introducer.

As illustrated in FIG. 9B, when the distal end 334 is in the open configuration, the upper and lower bend angles $\varepsilon_1$, $\varepsilon_2$, is 180° with respect to the main body 338. The upper bend 326, therefore, is parallel to each of the longitudinal axis 317 and the lower bend 328. While particular angles have been described for the upper and lower bend 326, 328 when the distal end 334 is in the open configuration, the bends of a dilator can comprise any suitable angle and skilled artisans will be able to determine suitable upper and lower bend angles based on various considerations, including the dimensions of a sheath and a dilator. Example angles considered suitable for an upper bend and/or a lower bend of a dilator when the dilator is in the open configuration include angles between about 160° and about 200°, angles between about 170° and about 190°, angles between about 175° and about 185°, and any other angle considered suitable for a particular embodiment.

As illustrated in FIG. 9B, when the distal end 334 is in the open configuration, each of the first and second transition angles $\phi_1$, $\phi_2$ is 160° with respect to the main body 338. Thus, just as each of the upper and lower bend angles $\varepsilon_1$, $\varepsilon_2$, changes between the open and closed configurations, each of the first and second transition angles $\phi_1$, $\phi_2$ changes between the open and closed configurations. While particular angles have been described for the first and second transition angles $\phi_1$, $\phi_2$ when the distal end 334 is in the open configuration, the bends of a dilator can comprise any suitable angle and skilled artisans will be able to determine suitable first and second transition angles based on various considerations, including the dimensions of a sheath and a dilator of an introducer. Example angles considered suitable for a first transition angle and a second transition angle of a dilator when the dilator is in the open configuration include angles between about 120° and about 200°, angles between about 150° and about 170°, angles between about 155° and about 165°, and any other angle considered suitable for a particular embodiment.

Figure 10A:
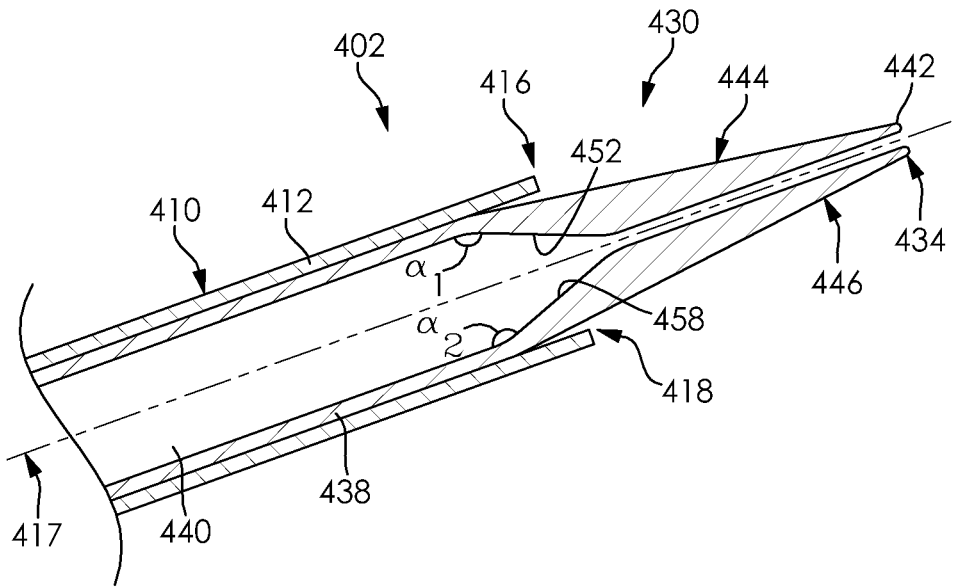
FIG. 10A is a partial cross-sectional view of the distal end of another embodiment of an introducer taken along a plane that is perpendicular to the longitudinal axis of the sheath. The distal end of the dilator is illustrated in the closed configuration.
Figure 10B:
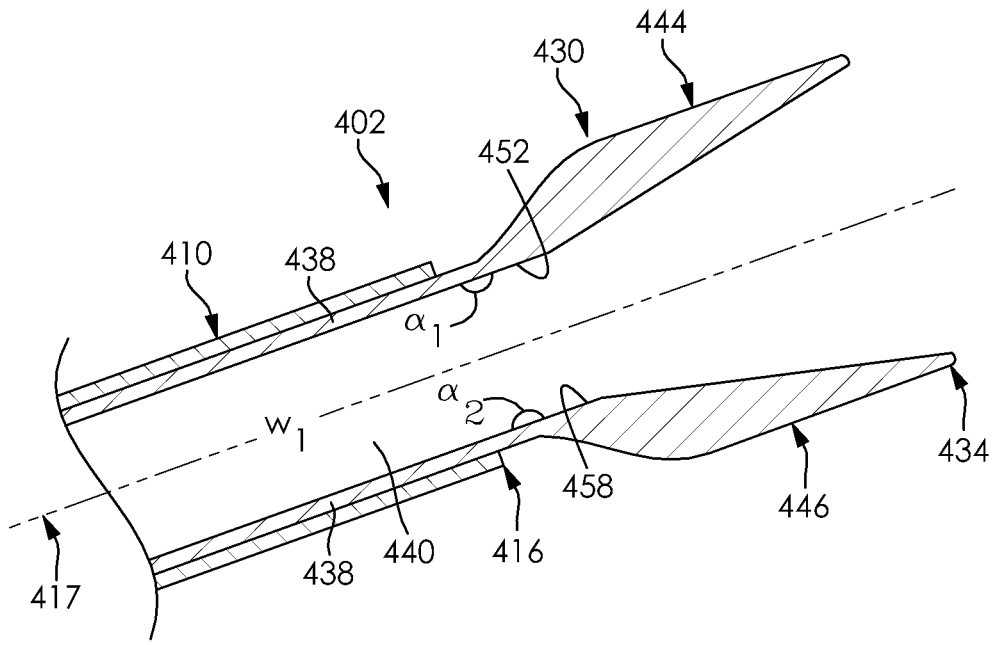
FIG. 10B is a view of the distal end of the introducer illustrated in FIG. 10A in which the distal end of the dilator is illustrated in the open configuration.

FIGS. 10A and 10B illustrate another example introducer 402. The example introducer 402 illustrated in FIGS. 10A and 10B is similar to introducer 2 illustrated in FIGS. 1 through 5B and described above, except as detailed below. Thus, the introducer 402 comprises a sheath 410 and a dilator 430. The sheath 410 has a main body 412, a distal end 416, a lumen 418, and a longitudinal axis 417. The dilator 430 is disposed within the lumen 418 and has a distal end 434, a main body 438, an inner passageway 440, a distal tip 442, a first lateral portion 444, and a second lateral portion 446.

In the illustrated embodiment, the dilator 430 is formed of a rigid, or semi-rigid material, such that the first lateral portion 444 and the second lateral portion 446 do not change their respective structural arrangements when moved between the open and closed configurations and are formed such that they are biased to the open configuration, as shown in FIG. 10B. When the sheath 410 is disposed over the dilator 430, as shown in FIG. 10A, the dilator 430 is in the closed configuration. In the closed configuration, the dilator 430 has first and second transition angles $\alpha_1$, $\alpha_2$ that indicate the degree to which the first and second transition portions 452, 458, respectively, taper inwardly from the main body 438 toward the distal end 434 and toward the longitudinal axis 417 of the sheath 410. The first and second transition angles $\alpha_1$, $\alpha_2$ are disposed where the main body 438 meets the first and second transition portions 452, 458, respectively. In the illustrated embodiment, each of the first and second transition angles $\alpha_1$, $\alpha_2$ is 160° relative to the main body 438 and the respective transition portions 452, 458. While the first and second transition angles $\alpha_1$, $\alpha_2$ have been described as being 160° in the closed configuration, the first and second transition angles of a dilator can be any suitable angle and skilled artisans will be able to select suitable first and second transition angles based on various considerations, including the dimensions of a sheath and a dilator of an introducer. Example angles considered suitable for each of the first and second transition angles relative to the main body and the respective transition portions when the dilator is in the closed configuration include angles between about 140° and about 180°, angles between about 150° and about 170°, angles between about 155° and about 165°, angles in which the first transition angle $\alpha_1$ is equal to, about equal to, greater than, or less than the second transition angle $\alpha_2$, and any other angle considered suitable for a particular embodiment.

In the open configuration, each of the first and second transition angles $\alpha_1$, $\alpha_2$ is 180° relative to the main body 438 and the transition portions 452, 458, respectively. While the first and second transition angles $\alpha_1$, $\alpha_2$ have been described as being 180° in the open configuration, the first and second transition angles of a dilator can be any suitable angle and skilled artisans will be able to select suitable first and second transition angles based on various considerations, including the dimensions of a sheath and a dilator of an introducer. Example angles considered suitable for each of the first and second transition angles relative to the main body and the respective transition portions when the dilator is in the open configuration include angles between about 160° and about 200°, angles between about 170° and about 190°, angles between about 175° and about 185°, angles in which the first transition angle $\alpha_1$ is equal to, about equal to, greater than, or less than the second transition angle $\alpha_2$, and any other angle considered suitable for a particular embodiment.

Figure 11A:
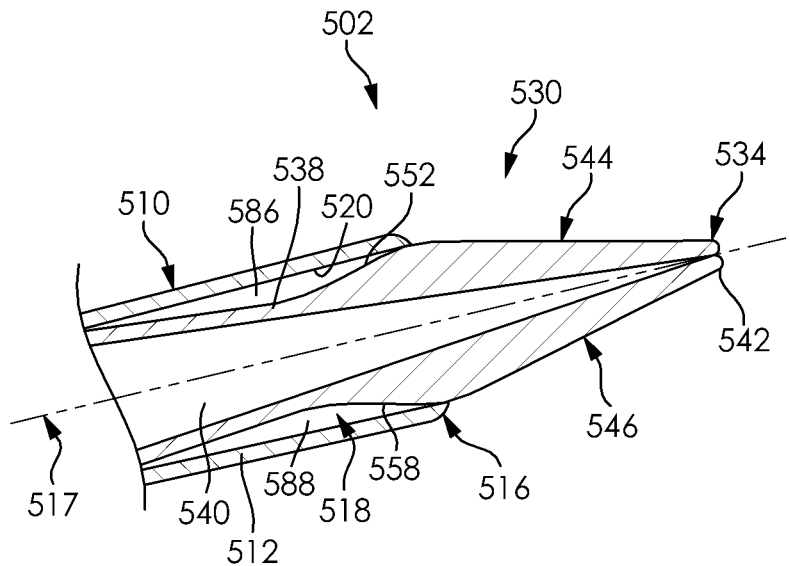
FIG. 11A is a partial cross-sectional view of the distal end of another embodiment of an introducer taken along a plane that is perpendicular to the longitudinal axis of the sheath. The distal end of the dilator is illustrated in the closed configuration.
Figure 11B:
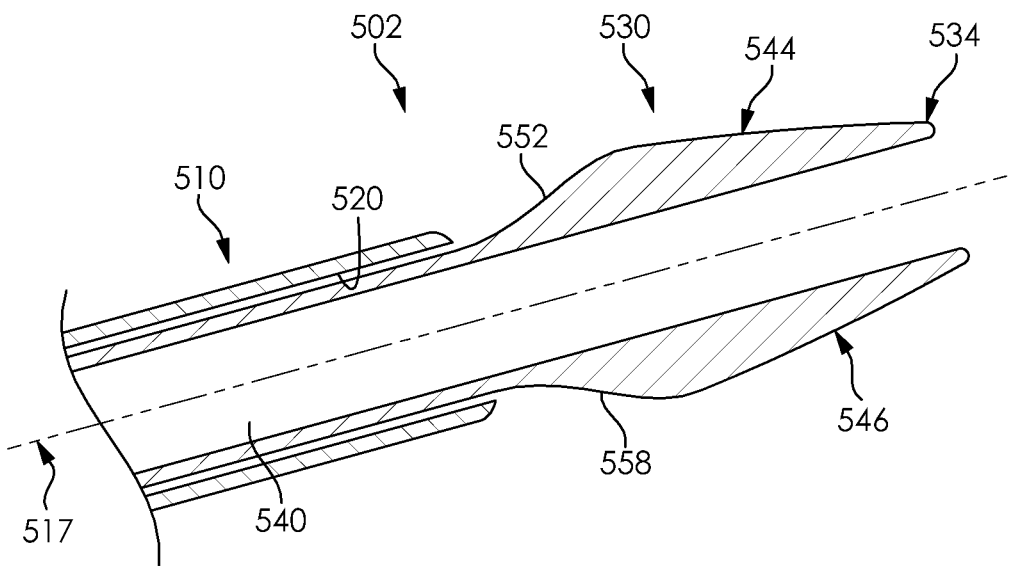
FIG. 11B is a view of the distal end of the introducer illustrated in FIG. 11A in which the distal end of the dilator is illustrated in the open configuration.

FIGS. 11A and 11B illustrate another example introducer 502. The example introducer 502 illustrated in FIGS. 11A and 11B is similar to introducer 402 illustrated in FIGS. 10A and 10B and described above, except as detailed below. Thus, the introducer 502 comprises a sheath 510 and a dilator 530. The sheath 510 has a main body 512, a distal end 516, a lumen 518, and a longitudinal axis 517. The dilator 530 is disposed within the lumen 518 and has a distal end 534, a main body 538, an inner passageway 540, a distal tip 542, a first lateral portion 544, and a second lateral portion 546.

In the illustrated embodiment, the first lateral portion 544 and the second lateral portion 546 are formed such that they are biased to the open configuration, as shown in FIG. 11B. However, alternative to being biased between the main body and the first and second lateral portions, as shown in FIGS. 10A and 10B, the dilator 530 is biased to the open configuration along its entire length. While the dilator 530 has been described as being biased to the open configuration along its entire length, a dilator can be biased to the open configuration along any suitable portion of its length and skilled artisans will be able to select a suitable length to bias a dilator based on various considerations, such as the materials that form the dilator. Example lengths considered suitable to bias a dilator to the open configuration include along the entire length of the dilator, half the length of the dilator, a quarter of the length of the dilator, and any other length considered suitable for a particular embodiment.

Each of the first transition portion 552 and second transition portion 558 is defined on a side of the dilator 530 disposed adjacent to the inner surface 520 of the sheath 510. As shown in FIG. 10A, in the closed configuration, the sheath 510 and the dilator 530 define an upper gap 586 and a lower gap 588. The gaps 586, 588 are empty spaces defined by the sheath 510 and dilator 530. The main body 538, the first transition portion 552, and the inner surface 520 of the sheath 510 define the upper gap 586. The main body 538, the second transition portion 558, and the inner surface 520 of the sheath 510 define the lower gap 588. In the illustrated embodiment, the dilator 530 and sheath 510 define each of the upper and lower gaps 586, 588 when the distal end 534 is in the closed configuration and neither of the upper and lower gaps 586, 588 is defined when the distal end 534 is in the open configuration, as shown in FIG. 11B.

In all embodiments, each of the components of the introducer may be formed of any suitable material, including presently known or later-developed materials for use in medical devices suitable for providing access to a body vessel. A skilled artisan will be able to select an appropriate material or appropriate materials for each component of an introducer discussed above based on various considerations including, but not limited to, the body vessel which a clinician seeks to access, the size and shape of a patient and his or her blood vessels and other body parts, and which, if any, medical devices the clinician wishes to use with a particular introducer embodiment. Examples materials considered suitable to form a dilator include, but are not limited to, biocompatible materials, materials that can be made biocompatible, metals such as stainless steel, polyetheretherketone, shape memory materials, shape memory alloys, polymers, shape memory polymers, nitinol, polyurethane, ethylene tetrafluoroethylene, polyether block amide, deformable materials, deformable memory materials, and any other material considered suitable for a particular embodiment. A dilator can be formed entirely of a single material or of multiple materials. For example, the distal end of a dilator (e.g., first lateral portion, second lateral portion, both the first and second lateral portions, distal portion extending from the dilator distal end toward the dilator proximal end) can be formed of a first material (e.g., nitinol) and the main body of the dilator (e.g., the proximal end, the proximal end to the first and second lateral portions, proximal portion extending from the dilator proximal end toward the dilator distal end) can be formed of a second material that is different than (e.g., stainless steel), or the same as the first material. The aforementioned materials that may form the dilator are intended to be illustrative in nature and do not limit the scope of the claims in any matter.

Examples materials considered suitable to form a sheath include, but are not limited to, biocompatible materials, materials that can be made biocompatible, metals such as stainless steel, polyetheretherketone, shape memory materials, shape memory alloys, polymers, shape memory polymers, nitinol, polyurethane, ethylene tetrafluoroethylene, polyether block amide, deformable materials, deformable memory materials, and any other material considered suitable for a particular embodiment. A sheath can be formed entirely of a single material or of multiple materials. For example, the distal end, or a distal portion that extends from the distal end toward the proximal end, of a sheath can be formed of a first material (e.g., nitinol) and a the proximal end, or a proximal portion that extends from the proximal end toward the distal end, of the sheath that is attached to the distal end, or distal portion, can be formed of a second material that is different than the first material (e.g., stainless steel), or the same as the first material. The aforementioned materials that may form the sheath are intended to be illustrative in nature and do not limit the scope of the claims in any matter.

Various methods of treatment are described herein. While the methods described herein are shown and described as a series of acts, it is to be understood and appreciated that the methods are not limited by the order of acts, as some acts may in accordance with these methods, occur in different orders, and/or concurrently with other acts described herein.

Figure 12:
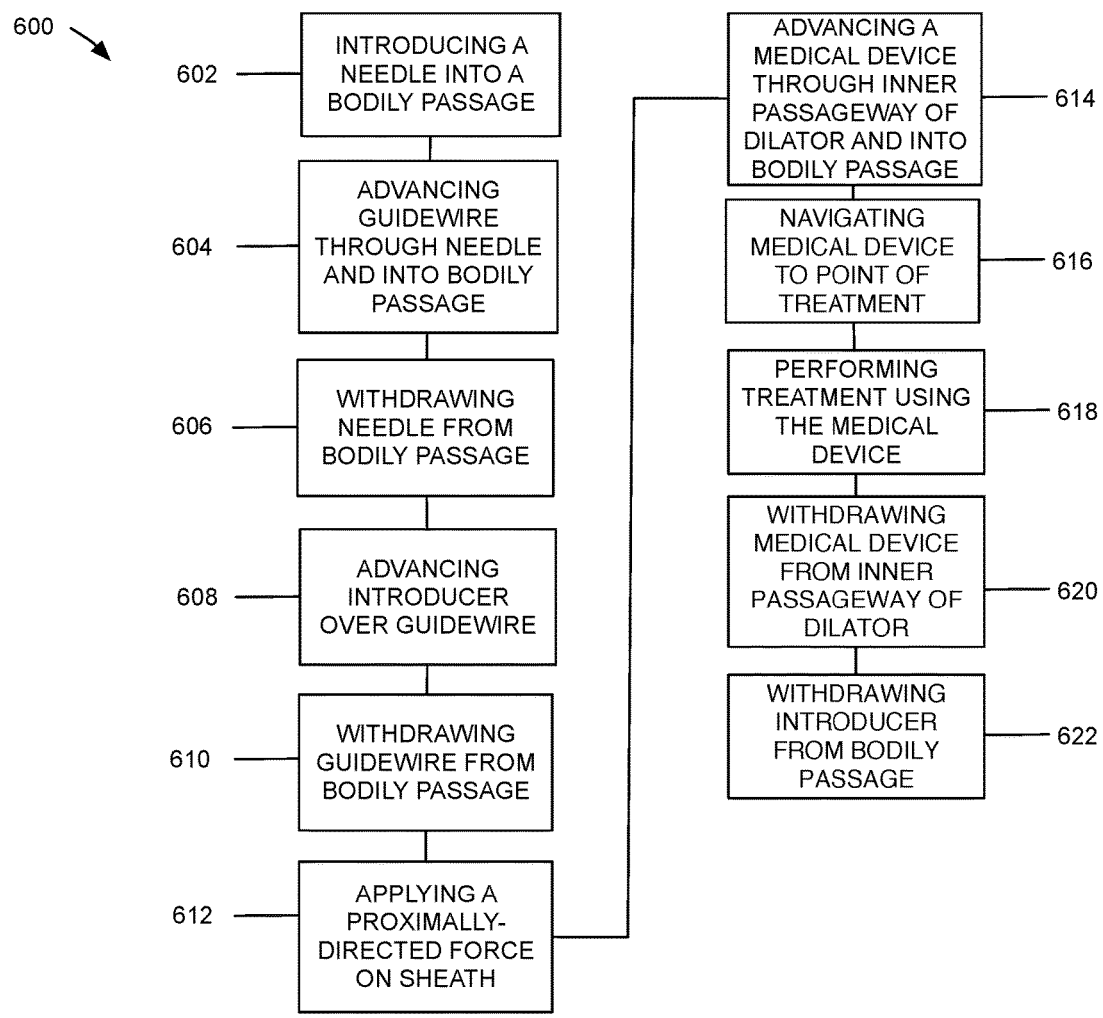
FIG. 12 is a flowchart representation of a method of using an introducer.

FIG. 12 is a flowchart representation of a method 600 of using an introducer.

A step 602 comprises introducing a needle having a needle proximal end, a needle distal end, and defining a needle lumen into a bodily passage such that the needle distal end is disposed within the bodily passage. The bodily passage is defined by a bodily passage wall. Another step 604 comprises advancing a guidewire having a guidewire proximal end and a guidewire distal end through the lumen defined by the needle such that the guidewire distal end is disposed within the bodily passage. Another step 606 comprises withdrawing the needle from the bodily passage such that the needle is passed over the guidewire and the needle distal end is disposed outside of the bodily passage. Another step 608 comprises advancing an introducer having an introducer proximal end and an introducer distal end over the previously-placed guidewire such that the introducer distal end is disposed within the bodily passage. The introducer comprises a sheath and a dilator. The sheath has a main body, a proximal end, a distal end, a lumen, and a longitudinal axis. The dilator is moveably disposed within the lumen of the sheath and has a proximal end, a distal end, a main body, an inner passageway, a distal tip, a first lateral portion, and a second lateral portion. Another step 610 comprises withdrawing the guidewire from the bodily passage. Another step 612 comprises applying a proximally-directed force on the sheath while maintaining the position of the dilator such that the sheath is advanced proximally over the dilator and the dilator moves from a closed configuration to an open configuration. In the open configuration, the first and second lateral portions of the dilator are free of the sheath and dilate the bodily passage. Another step 614 comprises advancing a medical device having a proximal end and a distal end through the inner passageway defined by the dilator such that the distal end of the medical device is disposed within the bodily passage. Another step 616 comprises navigating the medical device to a point of treatment within the bodily passage. Another step 618 comprises performing treatment using the medical device. Another step 620 comprises withdrawing the medical device from the inner passageway of the dilator such that the distal end of the medical device is free of the dilator and the bodily passage. Another step 622 comprises withdrawing the introducer from the bodily passage.

Step 602 can be accomplished using any suitable needle having any suitable length and structural arrangement. Skilled artisans will be able to select a needle to introduce into a bodily passage according to a particular embodiment based on various considerations, including the treatment intended to be performed. Step 602 can be accomplished by applying a distally-directed force (e.g., toward the bodily passage) on any suitable portion of the needle such that the needle distal end is advanced into the bodily passage.

Step 602 can be accomplished by introducing a needle into any suitable bodily passage. Skilled artisans will be able to select a suitable bodily passage to introduce a needle according to a particular embodiment based on various considerations, including the treatment intended to be performed. Example bodily passages considered suitable to introduce a needle include the urinary tract, any portion of the vascular system, a blood vessel, an artery, a vein, and any other bodily passage considered suitable for a particular embodiment.

Step 604 can be accomplished using any suitable guidewire having any suitable length and structural arrangement. Skilled artisans will be able to select a guidewire to introduce into a bodily passage according to a particular embodiment based on various considerations, including the treatment intended to be performed. Step 604 can be accomplished by applying a distally-directed force (e.g., toward the bodily passage) on any suitable portion of the guidewire such that the guidewire distal end is passed into and through the lumen defined by the needle and is advanced into the bodily passage.

Step 606 can be accomplished by applying a proximally-directed force (e.g., away from the bodily passage) on any suitable portion of the needle while maintaining the position of the guidewire such that the needle is passed over the guidewire, the distal end of the needle is withdrawn from, and is free of, the bodily passage, and the needle is free of the guidewire.

Step 608 can be accomplished using any suitable introducer according to an embodiment, such as the embodiments described herein. Skilled artisans will be able to select a suitable introducer to advance over a guidewire according to a particular embodiment based on various considerations, including the treatment intended to be performed. Examples of introducers considered suitable to complete one or more steps and/or methods described herein include introducers that include a sheath and a dilator that defines an inner passageway that extends from the proximal end of the dilator to the distal end of the dilator. Any of the introducers described herein, such as introducer 2, introducer 102, introducer 202, introducer 302, introducer 402, introducer 502, introducers that include the alternative components and/or configurations described herein, are considered suitable.

Step 608 can be accomplished by passing the proximal end of the guidewire through a distal opening of the inner passageway defined by the dilator (e.g., inner passageway 140 of dilator 130) and applying a distally-directed force (e.g., toward the bodily passage) on any suitable portion of the introducer such that the distal end of the introducer is passed over the previously-placed guidewire and is advanced into the bodily passage. An introducer can be advanced into the bodily passage until the distal end of the introducer is disposed at a point of treatment or distal to a point of treatment.

Step 610 can be accomplished by applying a proximally-directed force (e.g., away from the bodily passage) on any suitable portion of the guidewire such that the guidewire is withdrawn from, and is free of, the bodily passage and the inner passageway defined by the dilator. Optionally, this step can be completed subsequent to, or concurrent with, step 612, step 614, step 616, step 618, step 620, or step 622. For example, depending on the treatment being performed, the step of withdrawing the guidewire can be accomplished concurrently with step 620 or 622. Alternatively, this step can be completed by applying a proximally-directed force (e.g., away from the bodily passage) on any suitable portion of the guidewire while maintaining the position of, or applying a distally-directed force on, the introducer, such that the guidewire is withdrawn from, and is free of, the bodily passage and the inner passageway defined by the dilator. Alternatively, a guidewire, and the steps associated with a guidewire, can be omitted from method 600.

Step 612 can be accomplished by applying a proximally-directed force (e.g., away from the bodily passage) on any suitable portion of the sheath while maintaining the position of the dilator such that the sheath is advanced proximally over the dilator and the first and second lateral portions of the dilator expand radially-outward relative to the longitudinal axis of the sheath and become free of the sheath and dilate the bodily passage. For example, a proximally-directed force can be applied to the main body of a sheath, the proximal end of a sheath, at a location between the proximal end and the distal end of a sheath, on a hub attached to a sheath, and any other location considered suitable for a particular embodiment. Movement of the sheath relative to the dilator is considered advantageous at least because it provides a mechanism for dilating the bodily passage at the location of the dilator. For example, if the first and second lateral portions of a dilator are positioned at a point of treatment, movement of the sheath proximally over the dilator while maintaining the position of the dilator allows dilation to occur at the point of treatment (e.g., in place) rather than distal to the point of treatment and maintains the location of the distal end of the introducer during use.

While step 612 is described as being accomplished by applying a proximally-directed force on the sheath while maintaining the position of the dilator, step 612 can alternatively be accomplished by applying a proximally-directed force on the sheath while concurrently applying a distally-directed force on the dilator, or by maintaining the position of the sheath while applying a distally-directed force on the dilator. Accomplishing step 612 using one of these alternative steps results in dilation occurring in a location in the bodily passage that is different from the location in which the first and second lateral portions were placed in step 608.

An optional step comprises applying a distally-directed force (e.g., toward the bodily passage) on any suitable portion of the sheath while maintaining the position of the dilator such that the sheath is advanced distally over the dilator and the first and second lateral portions of the dilator contract radially-inward relative to the longitudinal axis of the sheath and become partially disposed within the lumen of the sheath. While this optional step is described as being accomplished by applying a distally-directed force on the sheath while maintaining the position of the dilator, this optional step can alternatively be accomplished by applying a distally-directed force on the sheath while concurrently applying a proximally-directed force on the dilator, or by maintaining the position of the sheath while applying a proximally-directed force on the dilator.

Step 614 can be accomplished by applying a distally-directed force on a medical device having a medical device proximal end and a medical device distal end such that the medical device distal end is introduced into and passed through the inner passageway of the dilator and into the bodily passage. This step can be accomplished using any suitable medical device, and skilled artisans will be able to select a suitable medical device to pass through the inner passageway of a dilator according to a particular embodiment based on various considerations, including the treatment intended to be performed. Example medical devices considered suitable to pass through the inner passageway defined by a dilator include suction catheters, balloon catheters, delivery devices, catheters having a stent disposed thereon, irrigation catheters, a camera, a light source, and any other medical device considered suitable for a particular application. Optionally, the medical device can be passed over a previously-placed guidewire in embodiments in which the guidewire is still present.

Step 616 can be accomplished by applying a force (e.g., distally-directed force and/or proximally-directed force) on the medical device until the medical device distal end is disposed at a point of treatment.

Step 618 can be accomplished by performing treatment using the medical device. Treatment can include any suitable treatment and can be based on the medical device passed through the dilator and skilled artisans will be able to select a suitable treatment to perform based on various considerations, including the medical device passed through an introducer. Example treatments considered suitable to perform include dilating a bodily passage, delivering a therapeutic agent within the bodily passage, delivering one or more medical devices at a point of treatment within the bodily passage (e.g., stent), and any other treatment considered suitable for a particular embodiment. For example, an optional step comprises advancing a balloon dilator with a stent disposed on the balloon through the inner passageway of a dilator and towards a point of treatment. Another optional step comprises passing a fluid into the balloon to move the balloon from a deflated configuration to an inflated configuration and to dilate the point of treatment and deliver the stent. Another optional step comprises stopping the passing of fluid into the balloon. Another optional step comprises removing a portion, or the entirety, of the fluid from the balloon. Another step comprises withdrawing the balloon catheter from the inner passageway of the dilator.

Step 620 can be accomplished by applying a proximally-directed force (e.g., away from the bodily passage) on any suitable portion of the medical device such that the medical device is withdrawn from, and is free of, the bodily passage and the inner passageway defined by the dilator.

Step 622 can be accomplished by applying a proximally-directed force (e.g., away from the bodily passage) on any suitable portion of the introducer such that the introducer is withdrawn from, and is free of, the bodily passage. Optionally, this step can be completed concurrently with step 620.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. An introducer, comprising:
  a sheath having a sheath proximal end, a sheath distal end, a sheath main body extending between the sheath proximal end and the sheath distal end, and a sheath longitudinal axis, the sheath main body defining a sheath lumen; and
  a dilator disposed within the sheath lumen and moveable between a closed configuration and an open configuration, the dilator having a dilator proximal end, a dilator distal end, a dilator main body extending between the dilator proximal end and the dilator distal end, and defining a dilator inner passageway, a first lateral portion, and a second lateral portion, the first and second lateral portions opposably positioned with respect to the sheath longitudinal axis, the first lateral portion having a first lateral portion inner surface and a first lateral portion thickness that tapers from a first location between the dilator proximal end and the dilator distal end toward the dilator distal end, the second lateral portion having a second lateral portion inner surface and a second lateral portion thickness that tapers from a second location between the dilator proximal end and the dilator distal end toward the dilator distal end, the first lateral portion inner surface contacting the second lateral portion inner surface when the dilator is in the closed configuration, the first lateral portion inner surface free from contact with the second lateral portion inner surface when the dilator is in the open configuration, the dilator having a first outside diameter at the distal end when the dilator is in the closed configuration and a second outside diameter at the distal end when the dilator is in the open configuration, the second outside diameter greater than the first outside diameter;

wherein proximally-directed movement of the sheath along the sheath longitudinal axis relative to the dilator results in movement of the dilator from the closed configuration to the open configuration and radially-outward movement of the first and second lateral portions relative to the sheath longitudinal axis.

2. The introducer of claim 1, wherein in the closed configuration the first lateral portion and the second lateral portion are adjacent and contacting each other and in the open configuration the first lateral portion and second lateral portion are spaced from each other with respect to the sheath longitudinal axis.

3. The introducer of claim 1, wherein the first lateral portion inner surface is disposed on a first plane that is substantially parallel to the sheath longitudinal axis when the dilator is in the closed configuration.

4. The introducer of claim 3, wherein the second lateral portion inner surface is disposed on a second plane that is substantially parallel to the sheath longitudinal axis when the dilator is in the closed configuration.

5. The introducer of claim 1, wherein first lateral portion and second lateral portion cooperatively define an opening on the dilator distal end when the dilator is in the closed configuration.

6. The introducer of claim 1, wherein each of the first lateral portion and second lateral portion has a first configuration when the dilator is in the closed configuration and a second configuration when the dilator is in the open configuration, the second configuration different than the first configuration.

7. The introducer of claim 1, wherein the dilator is biased to the open configuration.

8. The introducer of claim 1, wherein each of the first lateral portion and second lateral portion is biased to the open configuration.

9. The introducer of claim 1, wherein the dilator is formed of a single material.

10. The introducer of claim 1, wherein the dilator is formed of at least two materials.

11. The introducer of claim 10, wherein the dilator has a dilator proximal portion extending from the dilator proximal end toward the dilator distal end, the dilator proximal portion formed of stainless steel; and wherein the dilator has a dilator distal portion extending from the dilator distal end toward the dilator proximal end, the dilator distal portion formed of a shape memory alloy.

12. The introducer of claim 1, wherein the dilator has a dilator length extending from the dilator proximal end to the dilator distal end;

wherein the sheath has a sheath length extending from the sheath proximal end to the sheath distal end; and wherein the dilator length is greater than the sheath length.

13. The introducer of claim 1, wherein the sheath has a third outside diameter; and wherein the second outside diameter is greater than the third outside diameter.

14. An introducer, comprising:

a sheath having a sheath proximal end, a sheath distal end, a sheath main body extending between the sheath proximal end and the sheath distal end, a sheath length extending from the sheath proximal end to the sheath distal end, and a sheath longitudinal axis, the sheath main body defining a sheath lumen and having a first outside diameter; and a dilator disposed within the sheath lumen and moveable between a closed configuration and an open configuration, the dilator having a dilator proximal end, a dilator distal end, a dilator main body extending between the dilator proximal end and the dilator distal end, a dilator length extending from the dilator proximal end to the dilator distal end, and defining a dilator inner passageway, a first lateral portion, and a second lateral portion, the dilator length greater than the sheath length, the first and second lateral portions opposably positioned with respect to the sheath longitudinal axis, the first lateral portion having a first lateral portion inner surface and a first lateral portion thickness that tapers from a first location between the dilator proximal end and the dilator distal end toward the dilator distal end, the second lateral portion having a second lateral portion inner surface and a second lateral portion thickness that tapers from a second location between the dilator proximal end and the dilator distal end toward the dilator distal end, the first lateral portion inner surface contacting the second lateral portion inner surface when the dilator is in the closed configuration, the first lateral portion inner surface free from contact with the second lateral portion inner surface when the dilator is in the open configuration, the dilator having a second outside diameter at the distal end when the dilator is in the closed configuration and a third outside diameter at the distal end when the dilator is in the open configuration, the third outside diameter greater than the first outside diameter and the second outside diameter;

wherein proximally-directed movement of the sheath along the sheath longitudinal axis relative to the dilator results in movement of the dilator from the closed configuration to the open configuration and radially-outward movement of the first and second lateral portions relative to the sheath longitudinal axis; and wherein in the closed configuration the first lateral portion and the second lateral portion are adjacent and contacting each other and in the open configuration the first lateral portion and second lateral portion are spaced from each other with respect to the sheath longitudinal axis.

15. The introducer of claim 14, wherein the first lateral portion inner surface is disposed on a first plane that is substantially parallel to the sheath longitudinal axis when the dilator is in the closed configuration; and wherein the second lateral portion inner surface is disposed on a second plane that is substantially parallel to the sheath longitudinal axis when the dilator is in the closed configuration.

16. The introducer of claim 14, wherein first lateral portion and second lateral portion cooperatively define an opening on the dilator distal end when the dilator is in the closed configuration.

17. The introducer of claim 14, wherein each of the first lateral portion and second lateral portion has a first configuration when the dilator is in the closed configuration and a second configuration when the dilator is in the open configuration, the second configuration different than the first configuration.

18. The introducer of claim 14, wherein the dilator is biased to the open configuration.

19. The introducer of claim 14, wherein each of the first lateral portion and second lateral portion is biased to the open configuration.

20. An introducer, comprising:
a sheath having a sheath proximal end, a sheath distal end, a sheath main body extending between the sheath proximal end and the sheath distal end, a sheath length extending from the sheath proximal end to the sheath distal end, and a sheath longitudinal axis, the sheath main body defining a sheath lumen and having a first outside diameter; and
a dilator disposed within the sheath lumen and moveable between a closed configuration and an open configuration, the dilator having a dilator proximal end, a dilator distal end, a dilator main body extending between the dilator proximal end and the dilator distal end, a dilator length extending from the dilator proximal end to the dilator distal end, and defining a dilator inner passageway, a first lateral portion, and a second lateral portion, the dilator length greater than the sheath length, the first and second lateral portions opposably positioned with respect to the sheath longitudinal axis and cooperatively defining an opening on the dilator distal end when the dilator is in the closed configuration, the first lateral portion having a first lateral portion inner surface and a first lateral portion thickness that tapers from a first location between the dilator proximal end and the dilator distal end toward the dilator distal end, the first lateral portion inner surface disposed on a first plane that is substantially parallel to the sheath longitudinal axis when the dilator is in the closed configuration, the second lateral portion having a second lateral portion inner surface and a second lateral portion thickness that tapers from a second location between the dilator proximal end and the dilator distal end toward the dilator distal end, the second lateral portion inner surface disposed on a second plane that is substantially parallel to the sheath longitudinal axis when the dilator is in the closed configuration, the first lateral portion inner surface contacting the second lateral portion inner surface when the dilator is in the closed configuration, the first lateral portion inner surface free from contact with the second lateral portion inner surface when the dilator is in the open configuration, the dilator having a second outside diameter at the distal end when the dilator is in the closed configuration and a third outside diameter at the distal end when the dilator is in the open configuration, the third outside diameter greater than the first outside diameter and the second outside diameter;
wherein proximally-directed movement of the sheath along the sheath longitudinal axis relative to the dilator results in movement of the dilator from the closed configuration to the open configuration and radially-outward movement of the first and second lateral portions relative to the sheath longitudinal axis; and
wherein in the closed configuration the first lateral portion and the second lateral portion are adjacent and contacting each other and in the open configuration the first lateral portion and second lateral portion are spaced from each other with respect to the sheath longitudinal axis.

* * * * *